(12) United States Patent
Khoshbin et al.

(10) Patent No.: US 12,304,811 B2
(45) Date of Patent: *May 20, 2025

(54) OZONE-BASED CONTAMINANT ERADICATION SYSTEM AND METHOD

(71) Applicant: Housh Khoshbin, Lake Zurich, IL (US)

(72) Inventors: Housh Khoshbin, Lake Zurich, IL (US); Harley J. Pattee, Ocala, FL (US)

( * ) Notice: Subject to any disclaimer, the term of this patent is extended or adjusted under 35 U.S.C. 154(b) by 924 days.

This patent is subject to a terminal disclaimer.

(21) Appl. No.: 17/328,212

(22) Filed: May 24, 2021

(65) Prior Publication Data

US 2021/0275985 A1 Sep. 9, 2021

Related U.S. Application Data

(60) Division of application No. 16/017,722, filed on Jun. 25, 2018, now Pat. No. 11,014,062, which is a
(Continued)

(51) Int. Cl.
*C01B 13/10* (2006.01)
*A61L 9/20* (2006.01)

(52) U.S. Cl.
CPC ............... *C01B 13/10* (2013.01); *A61L 9/20* (2013.01); *A61L 2209/11* (2013.01); *A61L 2209/212* (2013.01)

(58) Field of Classification Search
None
See application file for complete search history.

(56) References Cited

U.S. PATENT DOCUMENTS

| 3,772,188 A | 11/1973 | Edwards |
| 4,124,467 A | 11/1978 | Pincon |
| (Continued) | | |

FOREIGN PATENT DOCUMENTS

| CN | 2768782 Y | * | 4/2006 | |
| GB | 2430275 A | * | 3/2007 | ......... H05B 41/2921 |
| (Continued) | | | | |

OTHER PUBLICATIONS

International Searching Authority Korean Patent Office, International Search Report and Written Opinion for PCT/US2009/031018 mailed Jul. 31, 2009.
(Continued)

*Primary Examiner* — Jennifer A Leung
(74) *Attorney, Agent, or Firm* — McDonald Hopkins LLC; James P. Muraff

(57) ABSTRACT

A device and method is provided for converting oxygen within air into ozone. The device has a portable housing with an air inlet and an enhanced ozone air outlet. A lamp housing is positioned within the portable housing and has a plurality of UV lamps for emitting UV radiation, the plurality of UV lamps extending from one end of the lamp housing to the other in a generally parallel configuration. The device also has a blower positioned within the portable housing for moving the air into contact with UV radiation from the plurality of UV lamps. The device further includes a plurality of baffles positioned within the lamp housing for dispersing the air as the air moves through the lamp housing. The device can be used to eliminate odors and contaminants found in the air, as well as to eliminate oils and contaminants found in water and to kill insects.

19 Claims, 27 Drawing Sheets

Related U.S. Application Data division of application No. 13/747,232, filed on Jan. 22, 2013, now Pat. No. 10,005,061, which is a continuation-in-part of application No. 13/632,944, filed on Oct. 1, 2012, now abandoned, and a continuation-in-part of application No. 12/014,033, filed on Jan. 14, 2008, now abandoned, said application No. 13/632,944 is a continuation-in-part of application No. 11/437,968, filed on May 19, 2006, now Pat. No. 8,277,740.

(60) Provisional application No. 60/683,258, filed on May 20, 2005.

(56) References Cited

U.S. PATENT DOCUMENTS

| | | | |
|---|---|---|---|
| 4,210,429 | A | 7/1980 | Golstein |
| 4,541,989 | A | 9/1985 | Foller |
| 4,672,271 | A * | 6/1987 | Gear ............ H05B 41/392 |
| | | | 315/117 |
| 4,857,277 | A | 8/1989 | Broomfield |
| 4,992,169 | A | 2/1991 | Izumiya |
| 5,219,534 | A | 6/1993 | Reynolds |
| 5,368,826 | A | 11/1994 | Weltz |
| 5,411,713 | A | 5/1995 | Wanaga |
| 5,501,844 | A | 3/1996 | Kasting |
| 5,601,786 | A | 2/1997 | Monagan |
| 5,660,719 | A | 8/1997 | Kurtz |
| 5,968,455 | A | 10/1999 | Brickley |
| 6,316,877 | B1 * | 11/2001 | Kaas ............ C02F 1/325 |
| | | | 315/56 |
| 6,426,053 | B1 | 7/2002 | Barnes |
| 7,326,387 | B2 | 2/2008 | Arts |
| 8,277,740 | B2 | 10/2012 | Pattee |
| 10,005,061 | B2 | 6/2018 | Khoshbin |
| 2002/0098109 | A1 | 7/2002 | Nelson |
| 2002/0104389 | A1 | 8/2002 | Hovey |
| 2003/0039577 | A1 | 2/2003 | Nelson |
| 2004/0047776 | A1 | 3/2004 | Thomsen |
| 2004/0061069 | A1 * | 4/2004 | Schalble ............ C02F 1/325 |
| | | | 250/432 R |
| 2004/0096354 | A1 | 5/2004 | Nomura |
| 2004/0120845 | A1 | 6/2004 | Potember |
| 2004/0146437 | A1 | 7/2004 | Arts |
| 2004/0161371 | A1 | 8/2004 | Russell |
| 2004/0259091 | A1 | 12/2004 | Yasuda |
| 2004/0265187 | A1 | 12/2004 | Davin |
| 2005/0170513 | A1 | 8/2005 | Moore |
| 2005/0214165 | A1 | 9/2005 | Babel |
| 2005/0226762 | A1 | 10/2005 | Naarup |
| 2006/0024196 | A1 | 2/2006 | Shimada |
| 2006/0144691 | A1 | 7/2006 | Barnes |
| 2006/0263238 | A1 | 11/2006 | Buhr |
| 2006/0263276 | A1 | 11/2006 | Pattee |
| 2007/0053806 | A1 | 3/2007 | Jo |
| 2007/0110629 | A1 | 5/2007 | Schmelz |
| 2007/0183931 | A1 | 8/2007 | Stock |
| 2008/0023330 | A1 | 1/2008 | Viovy |
| 2008/0030144 | A1 * | 2/2008 | Steckling ............ H05B 41/34 |
| | | | 315/224 |
| 2008/0107562 | A1 | 5/2008 | Hayashi |
| 2008/0253941 | A1 | 10/2008 | Wichers |
| 2009/0011451 | A1 | 1/2009 | Rodriguez |
| 2009/0035180 | A1 | 2/2009 | Wan |
| 2009/0068068 | A1 | 3/2009 | Harris |
| 2009/0117002 | A1 | 5/2009 | Kotov |
| 2009/0148847 | A1 | 6/2009 | Kokoris |
| 2009/0180934 | A1 | 7/2009 | Khoshbin |
| 2009/0217651 | A1 | 9/2009 | Jobson |
| 2009/0220388 | A1 | 9/2009 | Monzyk |
| 2009/0266702 | A1 | 10/2009 | Kambe |
| 2010/0006008 | A1 | 1/2010 | Sakamoto |
| 2010/0077650 | A1 | 4/2010 | Shiode |
| 2013/0028793 | A1 | 1/2013 | Pattee |
| 2018/0304226 | A1 | 10/2018 | Khoshbin |

FOREIGN PATENT DOCUMENTS

| | | | |
|---|---|---|---|
| JP | 07-313581 | | 12/1995 |
| JP | 2004232944 A * | | 8/2004 |
| KR | 10-2003-0071697 | | 9/2003 |
| WO | WO-9709073 A1 * | 3/1997 | ............ A61L 9/20 |
| WO | WO2005/021135 | | 3/2005 |
| WO | WO2009/091839 | | 7/2009 |

OTHER PUBLICATIONS

Philip Barlow, "An Introduction to Ozone Generation", in Technical Director—Watertec Engineering Pty Ltd., pp. 1-16, believed to be published in 1994.

\* cited by examiner

OZONE-BASED CONTAMINANT ERADICATION SYSTEM AND METHOD

CROSS-REFERENCE TO RELATED APPLICATIONS

This application is a divisional of U.S. patent application Ser. No. 16/017,722, which was filed on Jun. 25, 2018, which is a divisional of U.S. patent application Ser. No. 13/747,232, which was filed on Jan. 22, 2013. U.S. patent application Ser. No. 13/747,232 is a continuation-in-part application of U.S. patent application Ser. No. 12/014,033, which was filed on Jan. 14, 2008 and U.S. patent application Ser. No. 13/632,944, which was filed on Oct. 1, 2012. U.S. patent application Ser. No. 13/632,944 is a continuation of U.S. patent application Ser. No. 11/437,968, which was filed on May 19, 2006 and issued as U.S. Pat. No. 8,277,740 on Oct. 2, 2012. U.S. patent application Ser. No. 11/437,968 claims benefit of provisional of U.S. Patent Application No. 60/683,258, which was filed on May 20, 2005. The contents of each of the above-identified patent applications are hereby incorporated by reference in their entireties.

FEDERALLY SPONSORED RESEARCH OR DEVELOPMENT

None.

TECHNICAL FIELD

The present invention relates to improved devices and methods for converting oxygen into ozone, which are used to destroy and eliminate odors and contaminants that are often found in air, such as bacteria, molds, spores, fungus, and viruses, as well as to eliminate oils and contaminants found in water and to kill insects, and more specifically, to devices and methods for producing high concentrations of ozone to clean indoor air, purify water, and destroy contaminants found on surface areas in unoccupied spaces.

BACKGROUND OF THE INVENTION

Each Ozone ($O_3$) molecule consists of three oxygen atoms. Ozone is a pale blue gas at standard temperature and pressure, with an odor detectable at concentrations between 0.0076 and 0.036 parts per million (ppm). Depending on geographic location, altitude and season, natural ozone concentrations range typically from 0.01 to 0.05 ppm. Ozone is considered an air pollutant at ground-level. The U.S. Food and Drug Administration prohibits devices that result in more than 0.050 ppm of ozone in occupied enclosed spaces.

Ozone is unstable at high concentrations and will convert to ordinary diatomic oxygen ($O_2$). As a result ozone has a short life span and cannot be stored and transported, and consequently it must be produced on site. Ozone generators were developed at least as early as 1857, and ozone has been used in a variety of industries as an oxidizer and sterilizer. For example, ozone has been found to have many industrial and consumer applications, such as cleaning indoor air and purifying water. Ozone has also been used to effectively disinfect drinking water, deodorize air and objects, kill bacteria on food and other surface areas, sanitize swimming pool and spa, clean air in industrial plants, manufacture chemical compounds, treat industrial waste, as well as several other industrial and consumer applications, including pest control. The required concentration of ozone to oxidize and sterilize depends on the use of the ozone and the desired results.

A number of machines that produce ozone for residential use have been developed. For example, U.S. Patent Application No. 2006/0263276 A1, the contents of which are hereby incorporated by reference in its entirety, discloses an ozone generator for generating ozone and using that ozone to clean indoor air, purify water and kill mold, spores and other organisms on surface areas in unoccupied spaces. The first embodiment of this ozone generator has a rectangular shaped housing with wheels, a hinged lid, an extendable handle, and a plurality of openings, including inlets and outlets for air and ozone. This generator further has a remote control unit that is connected to the generator by a cable connection, which allows the user to turn the generator on and off from a remote location. The '276 application further discloses that the ozone generator includes a rectangular housing with a plurality of openings to allow the flow of oxygen into the generator and flow of ozone out of the generator. The housing also includes a lamp housing holding ultraviolet (UV) lamps, as well as a blower. This ozone generator has several practical limitations. For example, air enters the ozone generator and is immediately placed in direct contact with the UV lamps rather than below the UV lamps, which has the disadvantage of possibly causing overheating of the system due to poor air circulation. Also, the '276 application discloses that ozone exits the ozone generator prior to reaching the top UV lamp of fully circulating within the lamp housing. Thus, when using the ozone generator disclosed in the '276 application, the air does not fully circulate about each UV lamp prior to exiting the lamp housing and ozone generator, which prevents optimal ozone conversion. In addition, the '276 application is also deficient in providing an optimal outlet and inlet arrangement, further preventing more efficient conversion of $O_2$ to $O_3$. The 'ozone generator within the '276 application is deficient in providing optimal temperature constraints to more effectively produce the necessary $O_3$ concentration levels for many ozone generator applications to be commercially feasible, or for which unnecessarily require many more ozone generators due to the deficient performance of each ozone generator. Thus, there is a continuing need for a more effective ozone generator. The present invention is provided to solve these and other problems.

SUMMARY OF THE INVENTION

The present invention is directed to an improved ozone generator that produces high concentrations of ozone, and a method for operating the ozone generator. In one embodiment, the ozone generator includes a portable housing with an air inlet and an ozone outlet, a rectangular ultraviolet housing that fits inside the portable housing, a blower contained within the portable housing, a set or plurality of baffles, a set or plurality of ballasts and a control unit with a timer for operating the generator. The generator may also be operated using a remote control unit that does not connect to the housing for the ozone generator. The baffles are provided to enhance air circulation while the air flows through the ultraviolet lamp housing, which results in greater ozone conversion.

In yet another embodiment, the ozone generator has a portable housing with an air inlet with a first diameter and an ozone outlet that has a second diameter; a cylindrical or tubular ultraviolet housing that fits inside the portable housing; a blower contained within the portable housing; a set of baffles; and a control unit with a timer for operating the generator. The generator may also be operated using a remote control unit that does not connect to the housing. The cylindrical ultraviolet housing comprises: an inlet; an outlet; a tube, wherein the tube has an inner wall and an outer wall, and the inner wall and outer wall have a distance between them, wherein the tube has a circumference; and a set of ultraviolet lamps that emit ultraviolet radiation, wherein the set of ultraviolet lamps are arranged equidistant around the circumference of the tube. The blower moves air into contact with radiation from the set of ultraviolet lamps.

In a further embodiment, is closed-loop control system for an ozone generator that produces ozone. The ozone generator and the control system have a portable housing with an air inlet and an ozone outlet; an ultraviolet housing that fits inside the portable housing; a controller having an control application therein, implemented using a microprocessor and software and/or a hard-wired logic circuit configuration, to optimize the production of ozone by the ozone generator. The closed loop controller can be programmed with a set point. When the controller receives an input signal, such as ozone concentration, the controller makes one or more comparisons of the input signal to the set point, and sends an output signal commensurate with the comparison. One output signal can be an output signal to a variable speed fan or blower contained within the portable housing, wherein the variable speed blower moves air into contact with radiation from the set of ultraviolet lamps. The variable speed blower operates at an adjustable or variable speed. The output signal can control one or more of the speed of the variable speed fan, the intensity of the UV lamps, the size of the opening (using an electrically adjustable value) or other controllable and adjustable elements that may affect ozone concentration. A control unit can also be provided with a timer for operating the generator. The input signal can be generated by a meter. The meter can be located proximate the ozone outlet. The meter can measures the concentration of ozone flowing out the ozone outlet. The meter sends the input signal to the closed loop controller for allowing for continuous "closed-loop" control of the concentration of ozone flowing out of the ozone outlet.

The invention is also directed to a method using an ozone generator that consists of the following steps. First, the ozone generator is placed in an unoccupied, enclosed space. The ozone generator comprises a portable housing with an air inlet and an ozone outlet, an ultraviolet housing that fits inside the portable housing, wherein the ultraviolet housing contains a set of ultraviolet lamps that emit ultraviolet radiation, a blower contained within the portable housing, and a control unit with a timer that is connected to the housing for operating the generator. Second, the control unit is placed outside of the enclosed space to allow the user to operate the ozone generator without being exposed to the high concentrations of ozone. Next, the power for the ozone generator is turned on. The user may set the timer so that the generator operates at a desired time interval to produce optimal ozone generation. The ozone generator is manually turned off or is automatically shut off after the unoccupied, enclosed space has been exposed to high concentrations of ozone for an optimal time. The ozone generator may be automatically shut off by the timer. In a closed-loop controller embodiment, the controller continuously monitors the ozone concentration flowing out of the ozone outlet and continuously adjusts one or more output devices, such as the fan speed, the intensity of the UV lamps and/or the size of an adjustable input value for optimizing the concentration of the ozone flowing out of the ozone outlet.

A better understanding of the objects, advantages, features, properties and relationships of the invention will be obtained from the following detailed description and accompanying drawings which set forth an illustrative embodiment and is indicative of the various ways in which the principles of the invention may be employed.

DETAILED DESCRIPTION

Figure 1:
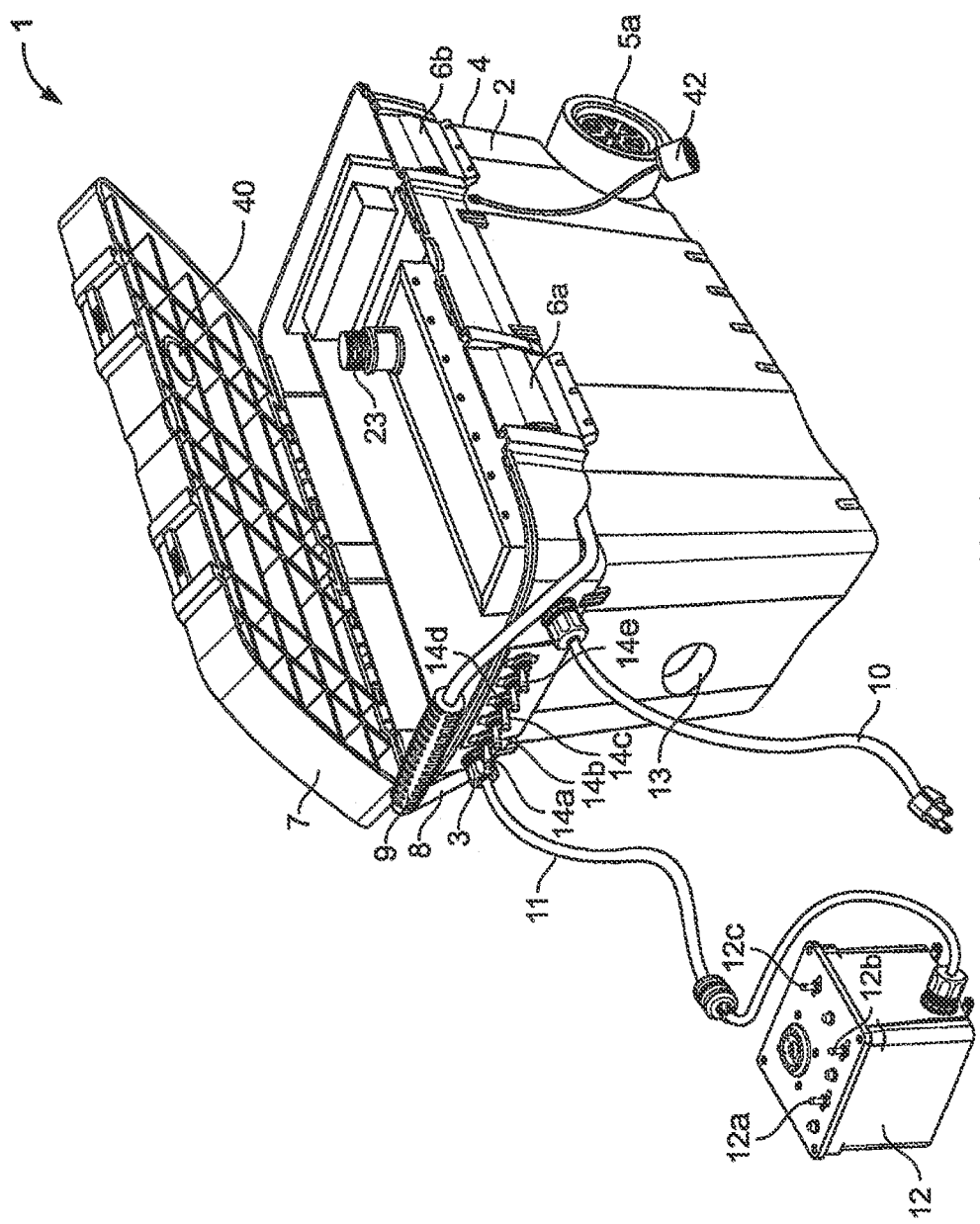
FIG. 1 is a front right perspective view of one embodiment of an ozone generator with an open lid.

An improved ozone generator and method of use are provided to produce all natural high concentrations of ozone that effectively destroy and eliminate odors and contaminants that are often found in air, such as bacteria, molds, spores, fungus, and viruses, as well as to eliminate oils and contaminants found in water and to kill insects. Depending on the configuration of the improved ozone generator, the ozone generator can produce concentrations of ozone up to and exceeding 200 parts per million (ppm). The improved ozone generator and method use the high concentrations of ozone to clean indoor air, purify water, and destroy contaminants found on surface areas in unoccupied spaces. The improved ozone generator and method is intended for use in unoccupied, enclosed spaces.

FIGS. 1 to 14 show one embodiment of an improved ozone generator that operates as a stand alone, portable ozone generator. An exemplary embodiment is shown in FIGS. 1 to 8 with different views of an ozone generator 1 that is a portable ozone generator unit having a rectangular shaped housing 2 with a front end 3 and a rear end 4. One skilled in the art would recognize that other shaped housing may be used, such as an octagon or square.

In FIG. 1 a housing 2 is shown that has wheels 5a and 5b on rear end 4. One skilled in the art would recognize that other known mobility-enhancing devices, such as rollers, may be used in place of wheels. Housing 2 is made from a plastic copolymer. Housing 2 has a hinged lid 7 that is kept securely closed by latches 6a and 6b. Hinged lid 7 has a circular opening 40 on its rear end for ozone outlet 23 to fit through when the hinged lid is closed. A cap 42 may be used to close circular opening 40 when the ozone generator 1 is not being used to protect the ultraviolet lamps. Cap 42 may be connected to housing 2 by a wire. Alternatively, circular opening 40 may be closed using an automatic shutter rather than cap 42. Housing 2 also has an extendable handle 8 on its front end 3 that allows ozone generator 1 to be moved by a pulling motion. Extendable handle 8 may have a grip 9 that makes pulling ozone generator 1 simpler and more comfortable for the user. Although not shown in FIGS. 1 to 14, a fixed handle may alternatively be used to move ozone generator 1.

FIG. 1 also shows a power cord 10 extending from front end 3. A cable connection 11 also extends from front end 3, and is used to connect a control unit 12 to ozone generator 1. Power cord 10 and cable connection 11 are attached to housing 2 through respective openings in housing 2. Housing 2 also has an air inlet 13 on front end 3 to allow for the flow of air into ozone generator 1. Air inlet 13 is centrally located below extendable handle 8. Air inlet has a 2⅝ diameter. In one embodiment, control unit 12 has toggle switches 12a, 12b, and 12c. Toggle switch 12a turns the power of ozone generator 1 on and off. Toggle switch 12b turns a timer 37 on and off. Toggle switch 12c allows a user to override settings of timer 37. Timer 37 may be any type of timer, including mechanical and digital timers. For example, timer 37 may be a 24-hour mechanical timer that has 15 minute setting intervals that allow a user to operate ozone generator 1 at 15 minute intervals over a 24-hour period. In another embodiment, front end 3 has toggle switches 14a, 14b, 14c, 14d, and 14e that turn ultraviolet lamps within housing 2 on and off. The number of toggle switches varies directly with the number of ultraviolet lamps used. One skilled in the art will understand that other types of switches could be substituted for the toggle switches. Although FIGS. 1, 2, 4, and 5 show cable connection 11, it is contemplated that a wireless remote control unit can also be used to operate ozone generator 1. For example, in one embodiment, ozone generator is operated using a remote control, so that the user is positioned outside of the enclosed space being treated and can operate the ozone generator safely from outside the enclosed space that is being treated. The use of a wireless remote control unit is advantageous because it eliminates the need for cable connection 11. Control unit 12 can also be used and placed inside the space being treated by setting timer 37 to turn on and off the generator.

Figure 2:
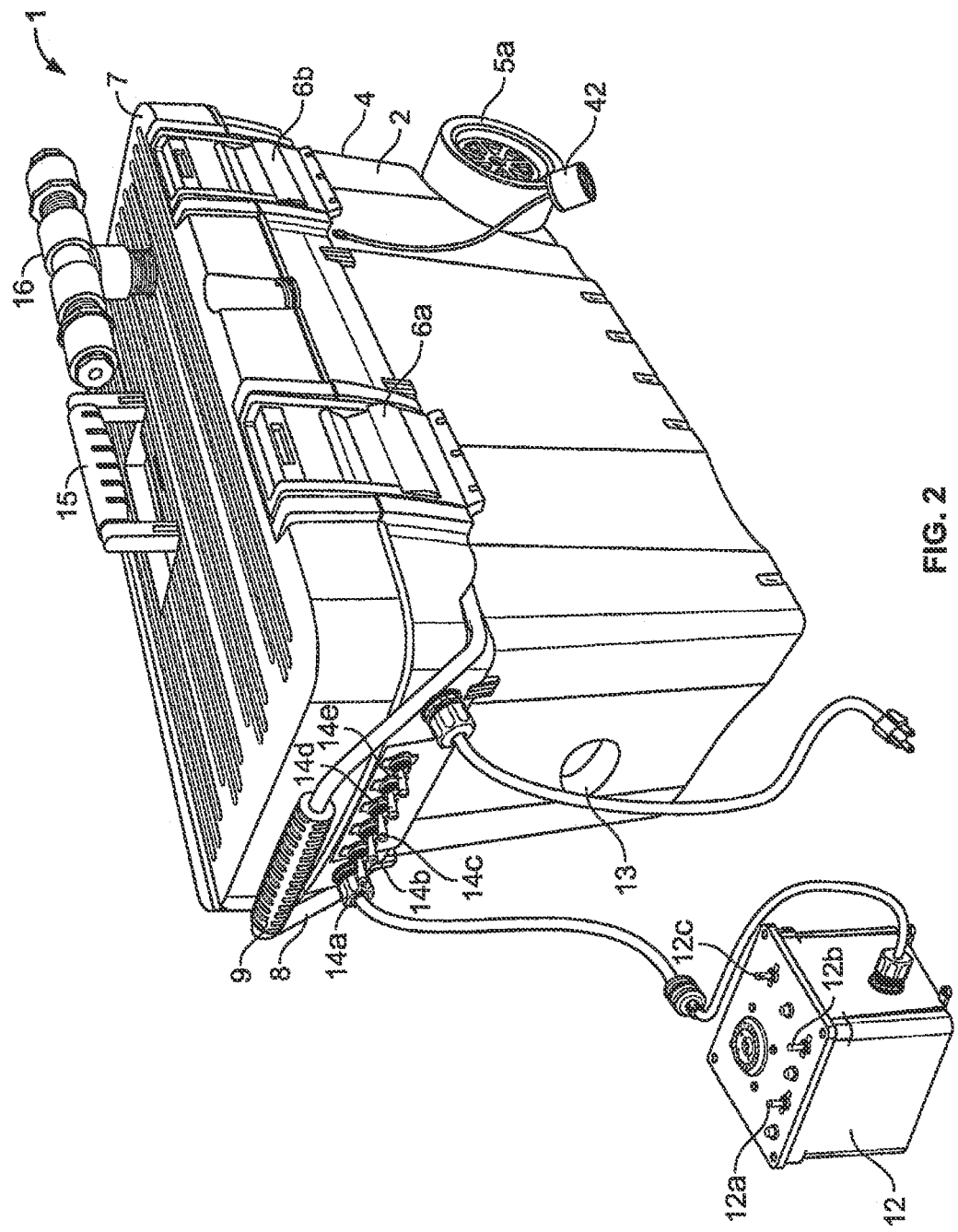
FIG. 2 is a front right perspective view of the ozone generator of FIG. 1 with a closed lid.

FIG. 2 has all of the elements of FIG. 1 and shows ozone generator 1 with hinged lid 7 in a closed position. A diverter 16 is shown in FIG. 2 that may be screwed onto ozone outlet 23 to allow for air with high concentrations of ozone to flow outside housing 2. Diverter 16 may be made from Schedule 80 piping. In an exemplary view, hinged lid 7 has a handle 15 that provides for lifting ozone generator 1.

Figure 3:
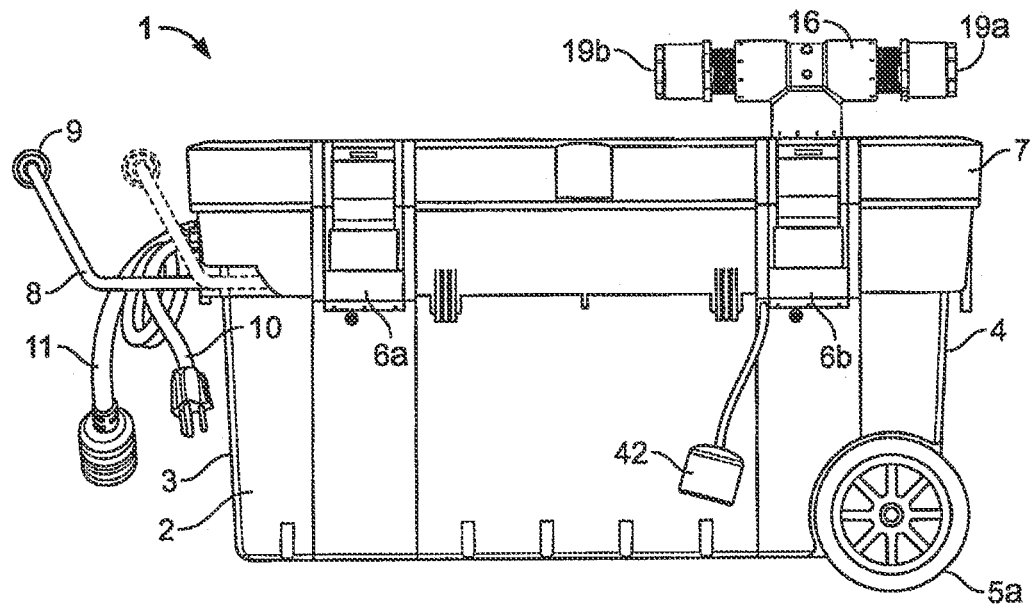
FIG. 3 is a right side elevation view of the generator of FIGS. 1 and 2 without hose connections.
Figure 4:
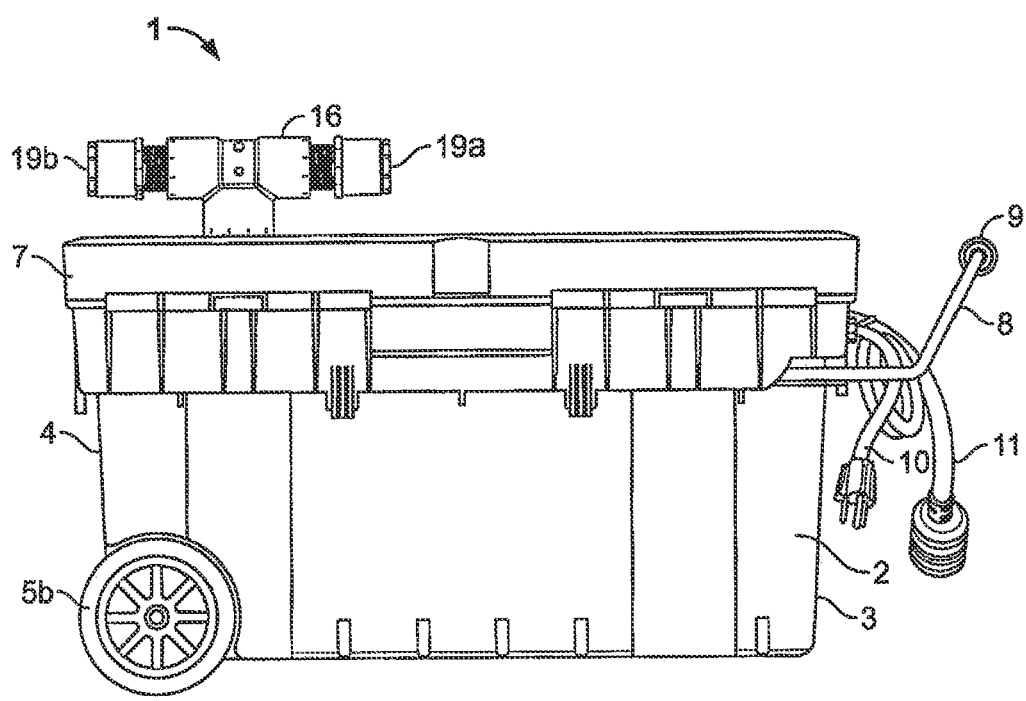
FIG. 4 is a left side elevation view of the generator of FIGS. 1 and 2 without hose connections.

FIG. 3 provides a view of the right side of ozone generator 1. The extendable function of extendable handle 8 is further illustrated in FIG. 3. FIG. 4 provides a view of the left side of ozone generator 1. In one embodiment, housing 2 is approximately 22 inches long, 16 inches high, and 14 inches wide. One skilled in the art would easily recognize other sizes and configurations for the unit housing and that the present invention is not limited to any specific dimensions.

Figure 5:
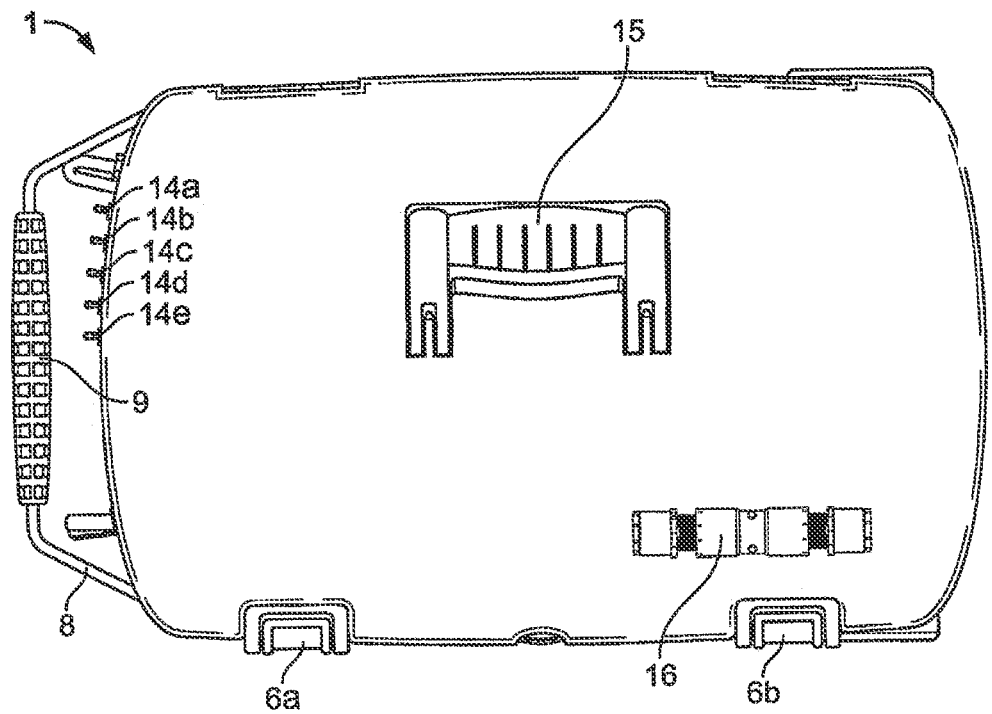
FIG. 5 is a top view of the generator of FIGS. 1 and 2.
Figure 6:
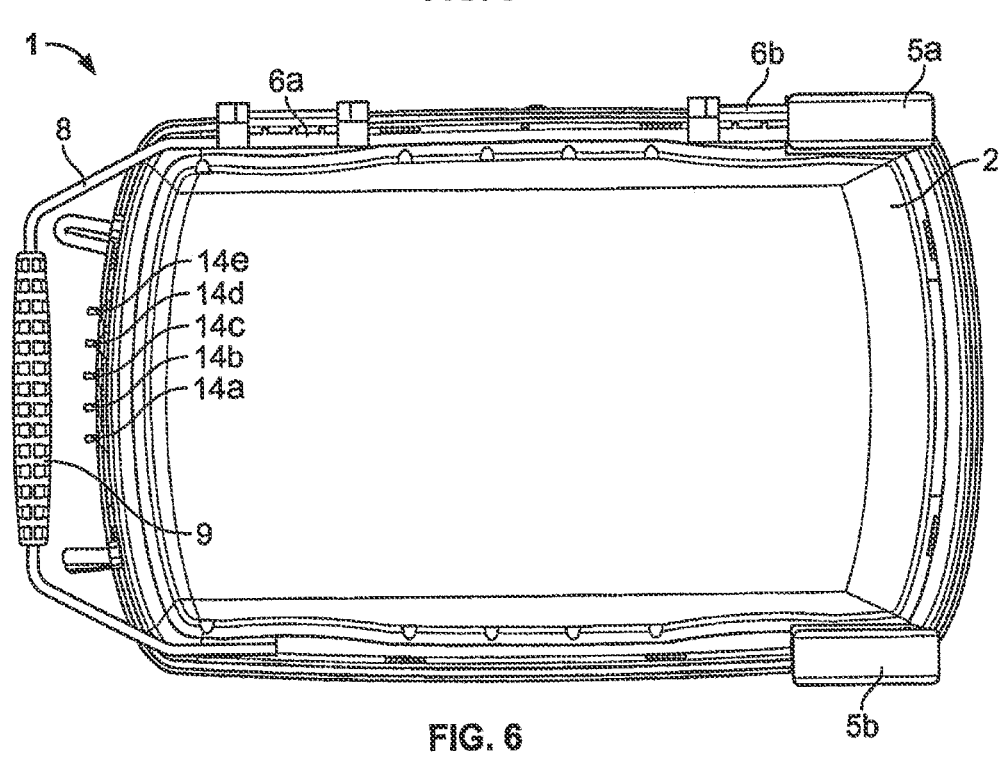
FIG. 6 is a bottom view of the generator of FIGS. 1 and 2.

FIG. 5 is a top view of ozone generator 1 with handle 15 and diverter 16 of FIG. 2. FIG. 6 shows the bottom side of ozone generator 1.

Figure 7:
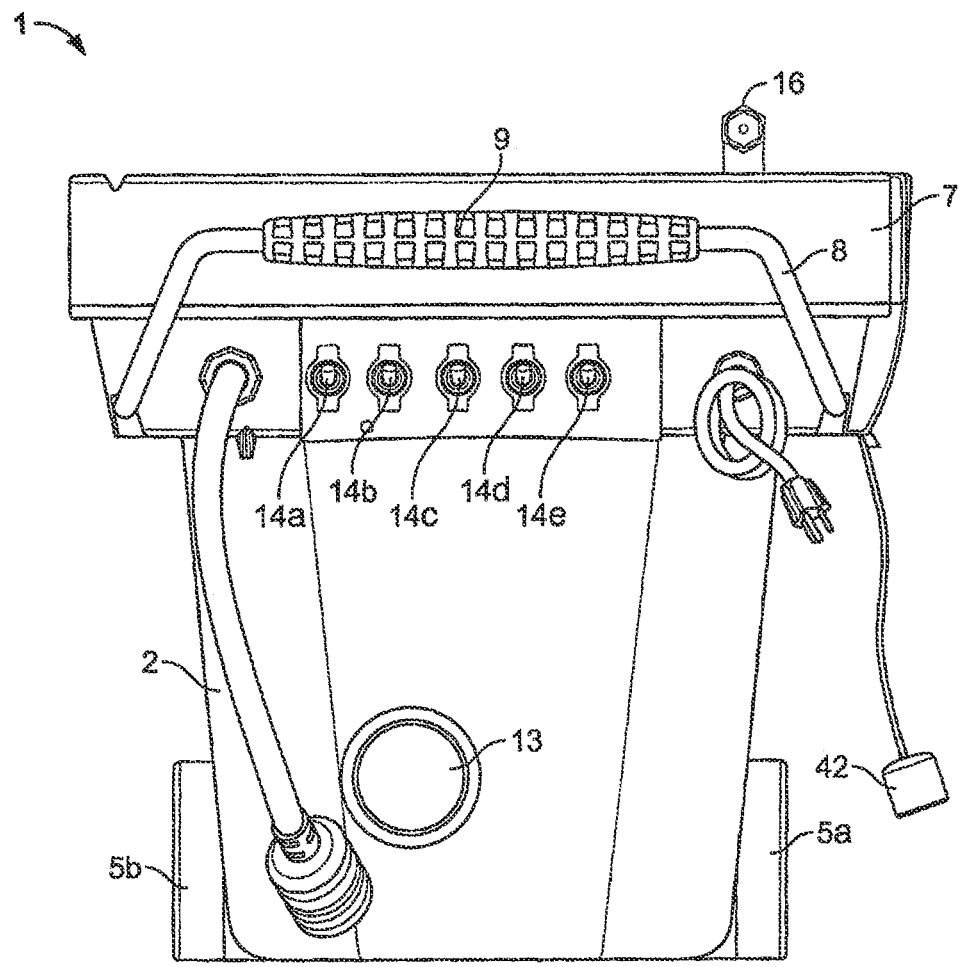
FIG. 7 is front elevation view of the generator of FIGS. 1 and 2.

FIG. 7 is a front elevation view of ozone generator 1 showing housing 2 with air inlet 13. In an exemplary embodiment, air inlet 13 is a circular orifice that is approximately 2⅝ inches in diameter. Air from the enclosed space to be treated enters air inlet 13, then proceeds to a blower 32 (not shown). Blower 32 causes the air to enter UV lamp housing 20 (not shown in this figure) at the inlet of the UV lamp housing 20, where the air is converted to ozone gas by the radiation omitted from the set of ultraviolet lamps 27 (not shown in this figure).

Figure 8:
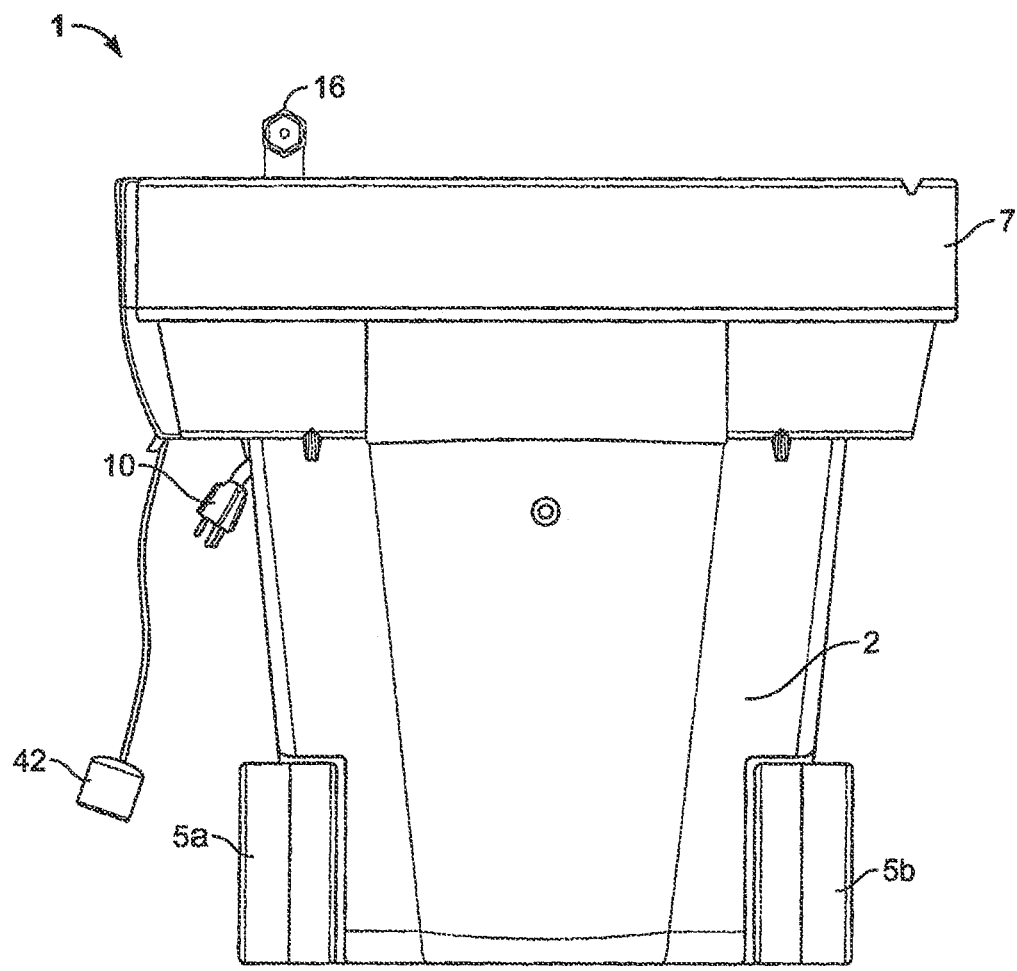
FIG. 8 is a rear elevation view of the generator of FIGS. 1 and 2.

FIG. 8 is a rear elevation view of ozone generator 1 showing housing 2 and diverter 16 for outbound ozone.

Figure 9:
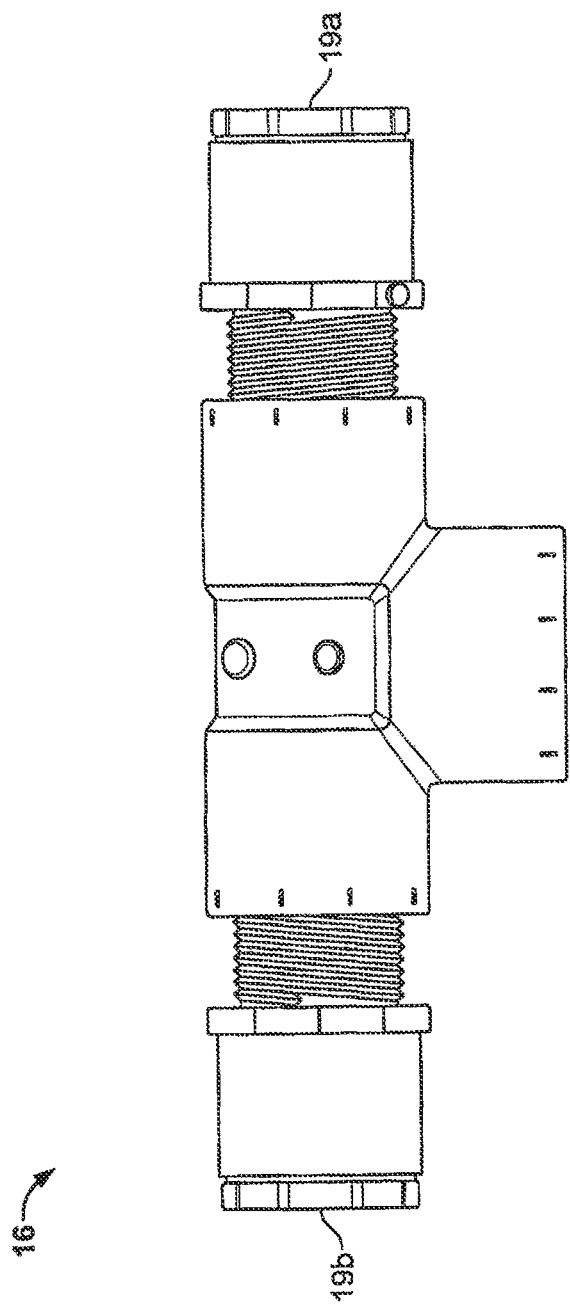
FIG. 9 is a front view of the diverter of FIG. 2.

FIG. 9 provides a front view of the diverter 16 of FIG. 2. When using ozone generator 1, hinged lid 7 is closed and diverter 16 is screwed onto ozone outlet 23. Diverter 16 has ozone outlets 19a and 19b for exit of ozone from ozone generator 1. Ozone outlets 19a and 19b provide back pressure to prevent dissipation of ozone prior to exiting ozone generator 1, and to ensure that the ozone has the highest concentration possible. Ozone outlets 19a and 19b have ⅜ inch diameters.

Figure 10:
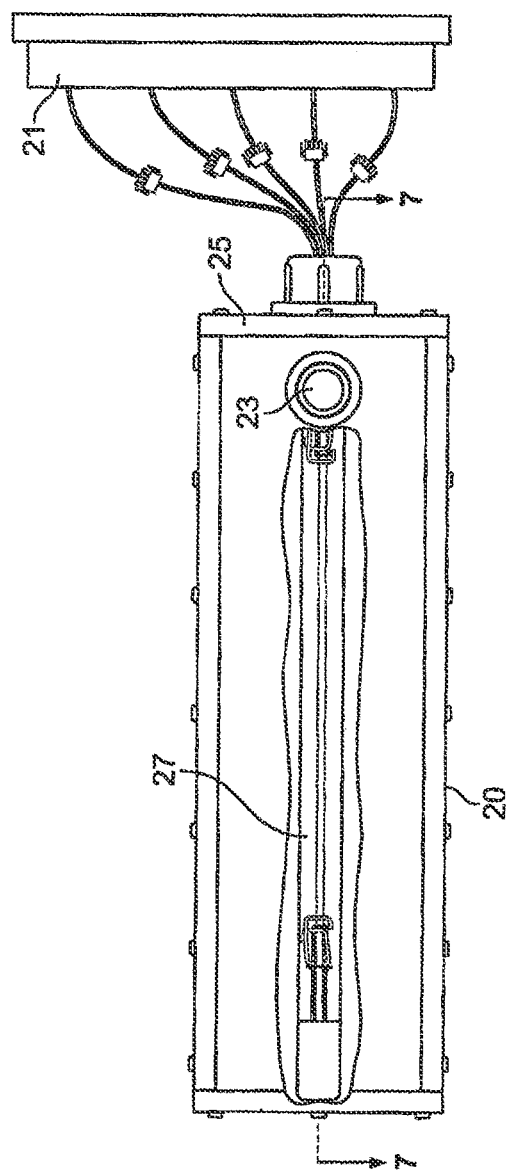
FIG. 10 is a top view of one embodiment of an ultraviolet lamp housing.

FIG. 10 is a top view of ultraviolet (UV) lamp housing 20 that is placed inside ozone generator 1. UV lamp housing 20 consists of a casing made from a polymer that surrounds a set of ultraviolet lamps 27. The casing's polymer may be polypropylene sheets. When viewed from the top, lamp ballast 21 is connected to rear end 24 of UV lamp housing 20 via connectors. Lamp ballasts may also be placed outside housing 2 rather than inside as shown in FIG. 10. The following table provides the electrical specifications for the connectors.

| Rated Wattage | 40 Watts |
| --- | --- |
| Operating Voltage | 86 Volts Nominal |
| Operating Current | 610 mA |
| UV Output @ 254 nm | 10 Watts |
| Intensity @ Meter | 95 Microwatts/cm² @ 0 hour |
| Rated Life | 9;000 hrs. |

Lamp ballasts provide the power for ultraviolet lamps 27 that are contained within UV lamp housing 20. The bottom of UV lamp housing 20 has an air inlet, and the top of UV lamp housing 20 has an ozone outlet 23. Preferably, air inlet is 2⅝ inches in diameter and ozone outlet is 1 inch in diameter. Air will enter air inlet at a flow rate of 100 cfm, and ozone will exit ozone outlet at a flow rate of 35 cm. However, the air inlet and ozone outlet vary depending on the size of the UV lamp housing, the type of blower used, and the number of ultraviolet lamps within the UV lamp housing.

Lamp ballasts 21 are also used to regulate the flow of power through the ultraviolet lamps. One lamp ballast is used per ultraviolet lamp that is housed within the UV lamp housing. The operating temperature by the ozone generator is 15 to 40° C. The optimal ambient temperature for lamps ranges from 20 to 25° C., and should be maintained consistent where ozone generator is operating. In order to ensure optimal circulation of air entering ozone generator 1 and maximize the conversion of air into ozone, it is essential that the ambient temperature of the UV lamps not exceed 40° C. Therefore, thermal switches are used on the lamp ballasts to allow the ozone generator's user to turn off the lamp ballasts when the operating temperature range exceeds 40° C. This feature of the invention prevents damage to the ozone generator while it is operating.

Figure 11:
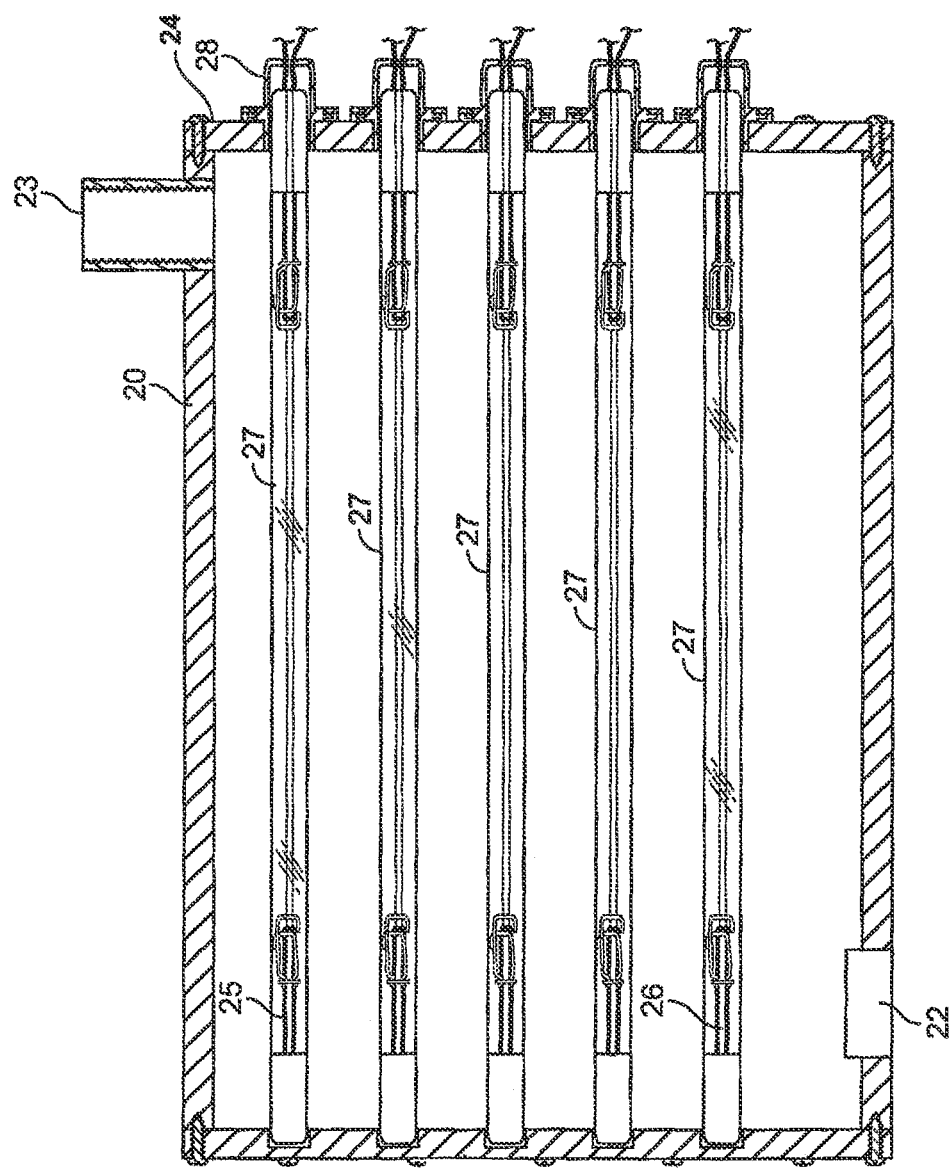
FIG. 11 is a cross-sectional side elevation view of the housing of FIG. 6 having five UV bulbs.

FIG. 11 is a cross-sectional side elevation view of UV lamp housing 20 of FIG. 6 taken along the indicated line. In an exemplary embodiment, the set ultraviolet lamps 27 has five ultraviolet lamps, each of which emits ultraviolet radiation, is positioned within the casing of UV lamp housing 20. The ultraviolet lamps are arranged vertically in parallel within the UV lamp housing with a top lamp 25 and a bottom lamp 26. This embodiment also provides for sets of ultraviolet lamps comprised of 1 to 20 lamps, but more lamps may be used with this ozone generator if desired, depending on blower type, inlet and outlet sizes, humidity, and temperature. The arrangement and spacing of the lamps is such that there is at least one inch between UV lamp housing 20 and top lamp 25, and at least two inches between UV lamp housing 20 and bottom lamp 26. In one embodiment, the space between each ultraviolet lamp within the set 27 of UV lamps is at least two (2) inches to ensure that the air circulates around each ultraviolet lamp prior to exiting outlet 23, preferably, the space between each ultraviolet lamp is two inches. The two inch spacing accommodates the air inlet 22 at the bottom, front of UV lamp housing 20, and ozone outlet at the top, and rear of UV lamp housing 20. Air inlet 22 is placed below bottom lamp 26, and ozone outlet 23 is placed above top lamp 25. Also shown in FIG. 11 are lamp connectors 28 that attach ultraviolet lamps 27 to lamp ballast 21 of FIG. 10.

Air enters air inlet 22 and flows around each lamp in the set of ultraviolet lamps 27 prior to exiting housing 20 from ozone outlet 23. Air is thus exposed to radiation from each ultraviolet lamp to allow the oxygen in the air to be converted into ozone when exposed to the radiation from the ultraviolet lamps. The ozone gas then exits the housing from ozone outlet 23, which must be placed above top lamp 25. The high concentration of ozone flows through the ozone outlet 23 into diverter 16, where it flows through ozone outlets 19*a* and 19*b* into the space being treated.

Figure 12:
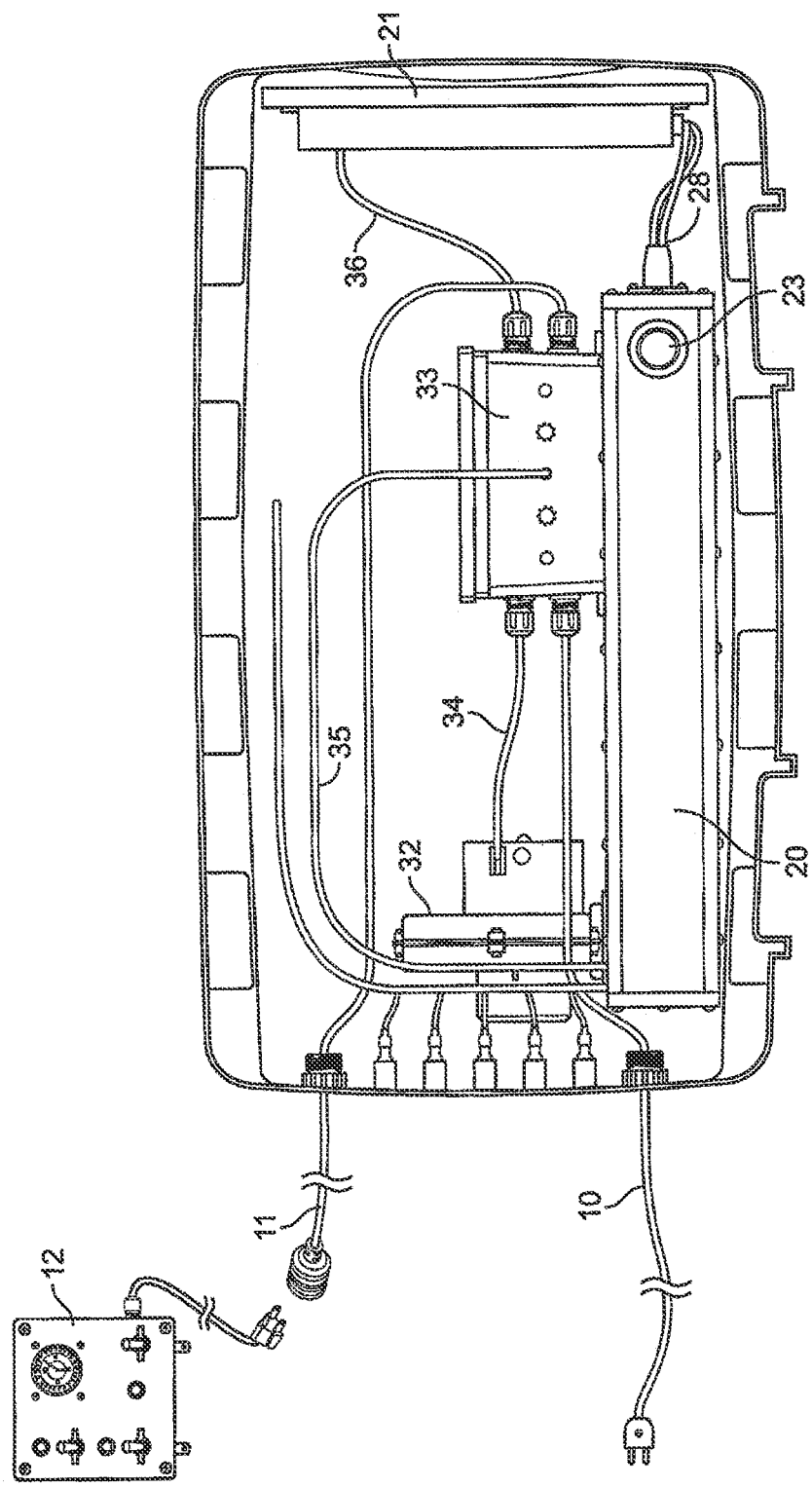
FIG. 12 is a top view of the generator of FIG. 1 with the lid off, showing interior details.

FIG. 12 shows the interior detail of the components of ozone generator 1 with hinged lid 7 removed. Blower 32 pulls air into ozone generator 1 through air inlet 13. An exemplary blower is one that is quiet and capable of moving one hundred (100) cubic feet of air per minute (100 cfm). Various fans can be used for implementing the present invention. In addition, a variable speed fan (with a variable speed drive) can be used to implement the present invention. These types of blowers/fans and drives are well known. One of ordinary skill would recognize that the type of blower used will vary with the size of the generator and number of ultraviolet lamps used. A wiring box 33 can be positioned adjacent the blower 32. The wiring box 33 can have a electrical connector 34 for wired connection of the wiring box 33 to the an auxiliary lamp housing assembly. The wiring box 33 can also have a connector 11 for wired connection of the wiring box 33 to a power cord 10 which provides power to the ozone generator. The wiring box 33 can also has a second connector 36 for wired connection of the wiring box to the UV lamp ballast(s) 21, and a third connector 35 for wired connection of the wiring box 33 to the lamp housing 20. In one embodiment, one side of the housing 2, toward the latch of the housing, contains UV lamp housing 20. The housing 2, toward the wheels, also contains the lamp ballast 21. Ozone generator has a set of baffles, such as in a rectangular shape, (not shown in FIG. 12) to redirect air flow in order to enhance air circulation within the lamp housing 20. Other baffle shapes, such as curved, winged, or other shapes and configurations, can be used to enhance air flow/circulation within the lamp housing. The use of baffles in the housing increases the probability that air will more fully circulate about the UV lamps and more efficiently be converted to ozone.

Figure 13:
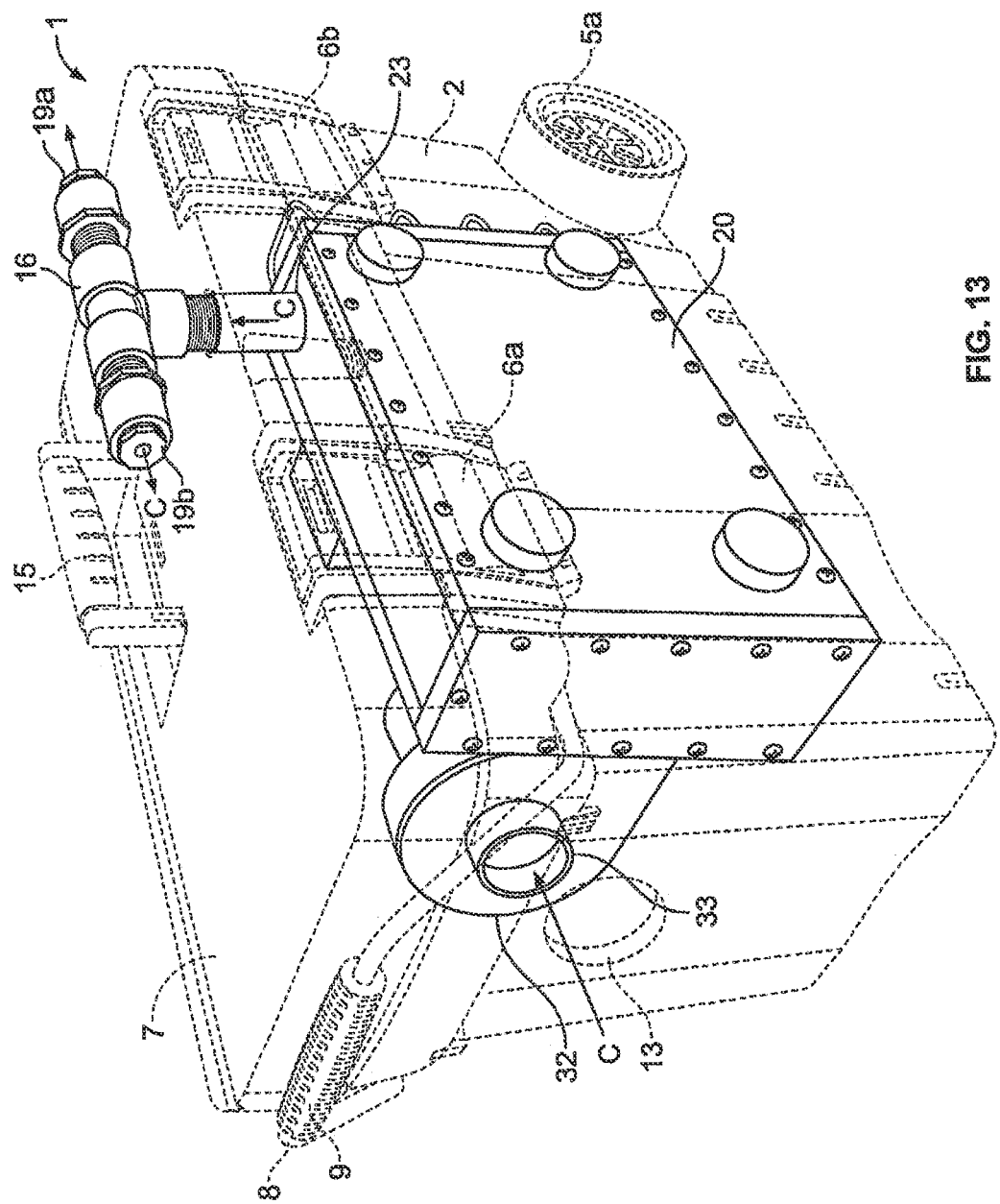
FIG. 13 is a front right perspective view of the generator of FIG. 3 with the phantomed housing.

FIG. 13 is a front right perspective view of ozone generator 1 with the housing 2 phantomed. An air inlet 13 is connected (in an air flow manner) to blower 32. Air flowing into ozone generator 1 is represented by arrow C. When ozone generator 1 is operating, air flows from the air inlet 13, by way of the blower 32, through the UV lamp housing 20. The UV light from the UV lamps interact with the air and ozone gas is produced at concentrations. In one embodiment the ozone concentration is at least 75 ppm of $O_3$.

Figure 14:
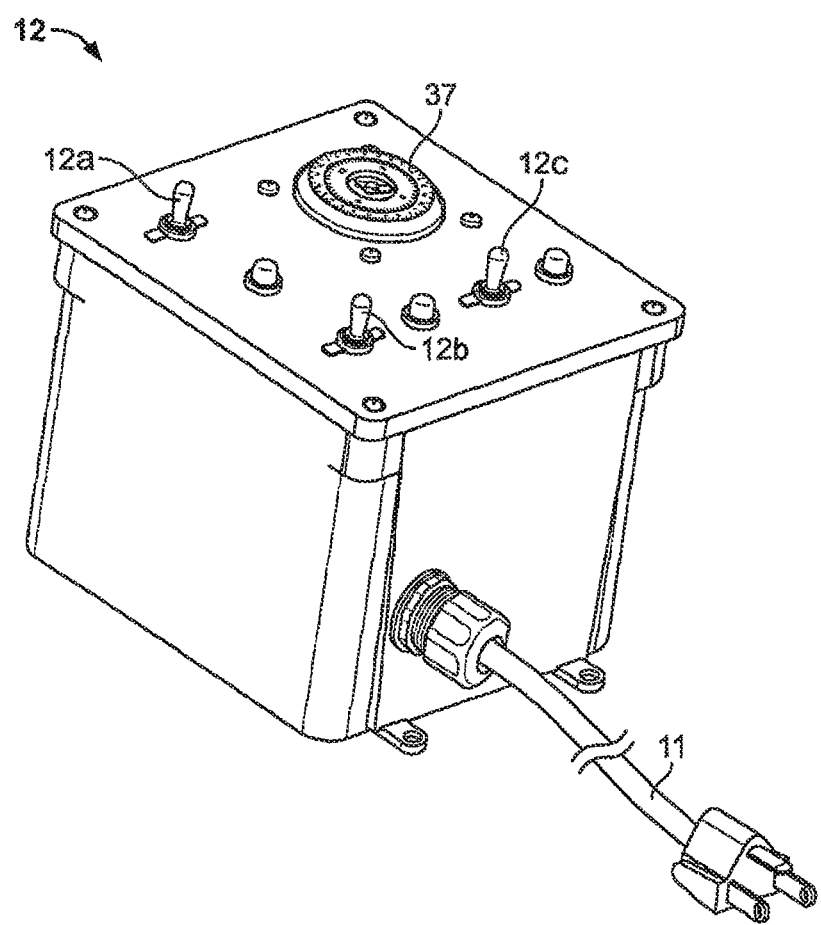
FIG. 14 is an enlarged perspective drawing of one embodiment of a timer/controller unit.

With continued reference to FIG. 1 and reference to FIG. 14, control unit 12 can be used to control the operation of ozone generator 1 by directly switching on or off blower 32, ultraviolet lamps 27, or other components, as desired. For example, FIG. 14 shows control unit 12 which is configured with timer 37 that can be set for starting and stopping the operation of ozone generator 1 from a remote location. As mentioned the control unit can be connected to the ozone generator housing via a wired connection. Each of three toggle switches 12*a*, 12*b*, 12*c* corresponds to and is electrically connected to an electrical connection in wiring box 23 and in one embodiment, is positioned next to a light which indicates when the switch is turned on and off. As described above, first toggle switch 12*a* turns on power, second toggle switch 12*b* turns on timer 27, and third toggle switch 12*c* provides an override function. The override function allows the user to keep the generator running despite the programmed setting for timer 37. Cable connector 11 is used to connect control unit 12 to ozone generator 1. In one embodiment, the cable is 50 feet long. Other lengths can be used, such as a longer length when the control unit 12 should be placed further away from the ozone generator, for at least safety concerns. Thus, the length may vary depending on the location of control unit 12 in relation to ozone generator 1.

In another embodiment, the ozone generator can include one or more controllers (not shown) having a control application running therein for controlling the operation of the ozone generator. The controller (in the housing) can be connected to all output devices and all input devices of the ozone generator, and control the operation of the output devices based on the signals and information received from the input devices. In one embodiment, a second controller can be connected to the switches and other input devices within the control unit 12 and can also be connected to the output devices within the control unit 12. The control unit 12 can also have an LCD display connected to the controller therein for displaying the current state, status and/or values of all input and output devices of the ozone generator, at any point in time during operation of the ozone generator. To provide this information to the remote control unit, such as the LCD display therein, in one embodiment, a first radio frequency (RF) transceiver can be connected to the controller within the ozone generator housing, and a second RF transceiver can be connected to the controller within the control unit 12, for transmitting information about the status of operation of the ozone generator from the controller within the housing to the controller within the control unit 12. The controller within the control unit 12 can then passes the status information to the LCD display within the control unit 12 for displaying such information to a user. The ozone generator can also have an LCD display connected to the controller therein, and visible from outside the housing of the ozone generator, for displaying the status of the operation of the ozone generator at any point in time, including the status, state and/or values of all of the input devices and output devices.

Figure 29:
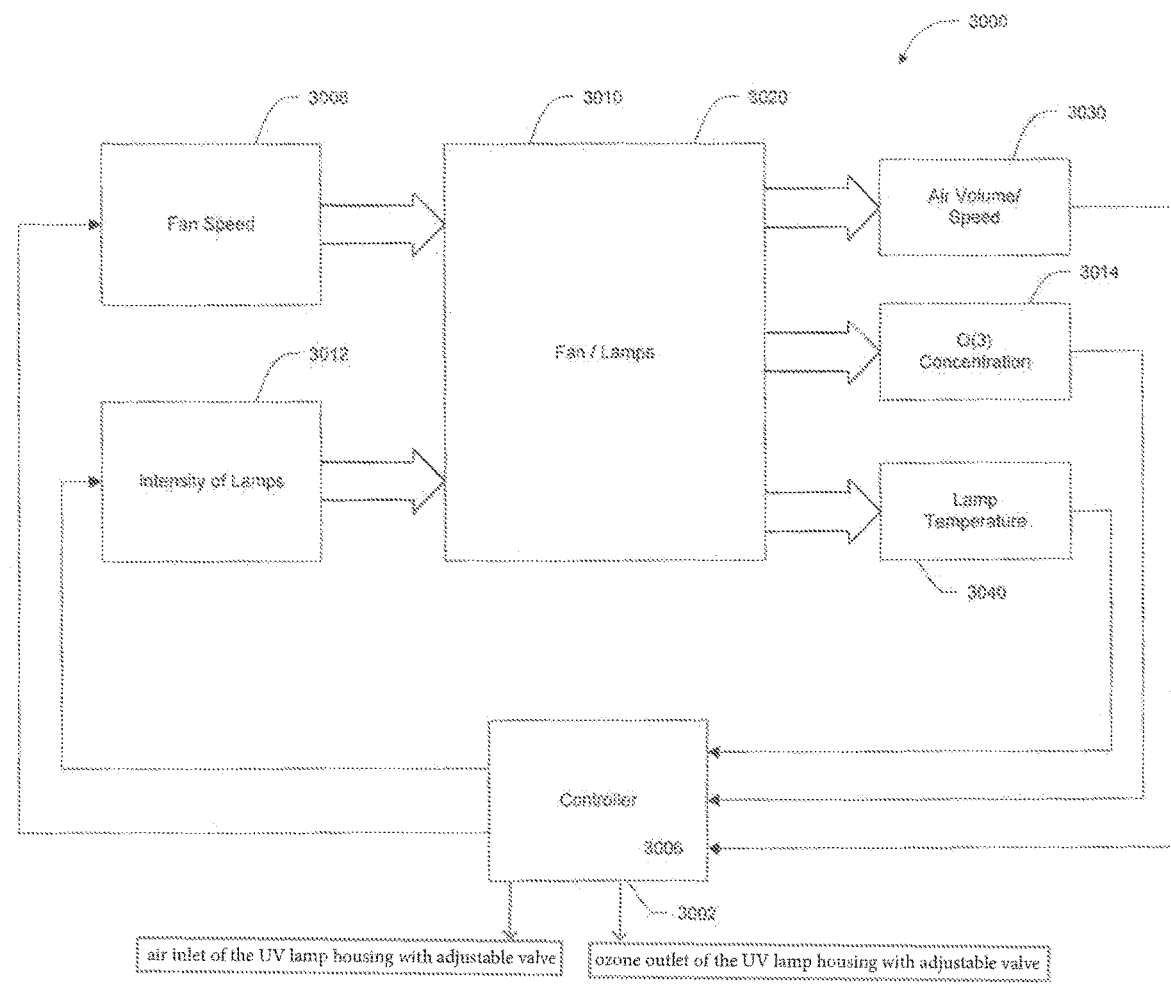
FIG. 29 is a functional flow diagram of another embodiment of the present invention.

Referring additionally to FIG. 29, the ozone generator 1 can also have a closed loop application running 3006 on or executing within the controller 3002, to automatically control the concentration of the ozone being generated by the ozone generator. Specifically, in one embodiment, the controller transmits a fan speed signal 3008 to the blower 3010 or fan to control the speed of the blower 3010 after determining the optimal speed for the blower 3010 based on one or more inputs, such as an ozone sensor or meter 3014 which can be positioned proximate the ozone outlet. Alternatively or additionally, the controller 3002 and the closed loop application 3006 therein can be configured to control the intensity of the UV lamps 3020 and/or an adjustable air inlet valve (not shown) at the air inlet of the ozone generator and/or an air outlet valve (not shown) at the air or ozone outlet of the ozone generator 1. The ozone meter 3014 measures the concentration of ozone or a variable which can be used by the controller to calculate the ozone level proximate the outlet, such as the amount of ozone in parts per million exiting the ozone generator. The meter continuously monitors the ozone level proximate the outlet, and the controller receives an input signal from the meter providing ozone generation level information, and as stated above continuously controls at least one of the outputs, such as the speed of the blower, the intensity of the UV lamps, the size of the inlet valve, and/or the size of the outlet valve, to optimize the ozone concentration exiting the ozone outlet, in a closed loop configuration.

For example, the controller 3002 and closed loop application 3006 therein, can be programmed with an algorithm which will reduce the speed of the blower 3008 when increasing/reducing the speed of the blower 3008 provides a reduced/increased concentration of ozone leaving the ozone outlet of the ozone generator, respectively. Likewise, the controller 3002 and closed loop application 3006 therein, can be programmed with an algorithm which will increase the speed of the blower 3008 when reducing/increasing the speed of the blower 3008 provides a reduced/increased concentration of ozone leaving the ozone outlet of the ozone generator, respectively. Similarly, the controller 3002 and closed loop application 3006 therein, can be programmed within an algorithm which will reduce the intensity of the UV lamps 3012 when increasing/reducing the intensity of the UV lamps 3012 reduces/increases the concentration of ozone leaving the ozone outlet of the ozone generator. Likewise, the controller 3002 and closed loop application 3006 therein, can be programmed within an algorithm which will increase the intensity of the UV lamps 3012 when increasing/reducing the intensity of the UV lamps 3012 increases/reduces the concentration of ozone leaving the ozone outlet of the ozone generator. A similar algorithm can be provided for controlling the size of inlet and/or outlet/ozone valve openings to provide optimal ozone concentration leaving the ozone generator 1. When there is no or little (less than a predetermined amount) affect on ozone concentration when an output signal provided to an output device from the controller is varied, the algorithm can be configured to maintain the output signal(s) to the output devices. In one embodiment, this maintaining of the current signals to the output devices is only performed if the controller has already determined that an increase of ozone concentration has increased more than a predetermined amount and/or the rate of (change) increase of the ozone concentration is greater than a predetermined rate of change amount. The algorithm(s) can be also be configured to include other derivative or integration control in order to tune or optimize the ozone concentration leaving the ozone generator 1. The controller 3002, control application 3006 and respective user interface can be configured to receive at least minimum and/or target ozone concentration set point parameters for the ozone generator to achieve. Utilizing minimum and/or target set points can assist in significantly reducing "hunting" for optimal ozone concentrations, especially when utilizing derivative and/or integration control.

The ozone generator 1 can also include other input devices to continuously measure variables such as air volume flow or air speed 3030 of air entering the air inlet and/or exiting the ozone outlet, and the controller 3002 and closed loop control application 3006 therein can similarly receive and use this information to determine the appropriate output signals to send or transmit to the one or more output devices to optimize the ozone being generated by the ozone generator 1. Likewise, the ozone generator 1 can also include further input devices to continuously measure variables such as UV lamp temperature or the temperature of the air proximate the lamps or within the lamp housing 3040, and the controller 3002 and closed loop control application 3006 therein can similarly receive and use this information to determine the appropriate output signals to send or transmit to the one or more output devices to optimize the ozone being generated by the ozone generator 1. In addition, the ozone generator 1 can further include input devices to continuously measure variables such as internal ozone generator humidity, external (working space) humidity, and/or humidity within lamp housing, and the controller 3002 and closed loop control application 3006 therein can similarly receive and use this information to determine the appropriate output signals to send or transmit to the one or more output devices to optimize the ozone being generated by the ozone generator 1.

The ozone generator 1 can also include a global positioning system (GPS) to allow users to easily track the location of the ozone generator. This feature is beneficial to at least owners of ozone generators that lease the ozone generators to third parties who treat various structures. A GPS receiver can be connected to the controller 3002 for providing the controller 3002 with the current location coordinates of the ozone generator 1. The ozone generator 1 can also include a radio frequency (RF) transmitter for communicating the current GPS location coordinates received by the controller to a remote communication device, such as a cellular network, the internet or other communication network, for further transmission to a client computer, cell phone, PDA, or other communication device that can be used to generate one or more ozone generator tracking interface screens. The tracking screens can include a mapping overlay, and can include ozone generator points (flags/icons) which indicate the identity of each specific ozone generator and the current location of each ozone generator. Each controller of each ozone generator 1 can also be configured to transmit status information to the communication network and onto the remote interface device, for displaying the status information for each respective ozone generator on one or more interface screens on the remote interface device. In one embodiment, the remote interface application generating the interface screens on the remote interface device can be configured to allow the user to click on or selected a particular ozone generator from the mapping (location) screen or other interface screen providing a list of the ozone generators 1 to choose from, and the stats information for the selected ozone generator 1 will appear a same or new interface screen. The status information communicated by the controller of the ozone generator and displayed on the remote interface screen of the remote device, can include for example, whether the ozone generator is currently turned on, whether the ozone generator is generating ozone, the ozone concentration of the ozone being generated by the ozone generator, the speed of the fan, intensity of the UV lamps, the size of the inlet and/or outlet, any temperatures being measured, any air speeds or volumes being measured, any humidity being measured, and/or any input values being measured, if in operation—the time that the ozone generator has been operating, a log of each of the above status information stored and displayed at predetermined intervals for the current (and previous) ozone generation jobs, a history of all of this status information for all prior ozone generation jobs, a schedule of where and when all prior jobs took place, and a scheduler for future jobs. The owner or the ozone generators can provide clients or customers remote access to this status information and other functions, such as scheduling functions, over the internet, through a direct dial up connection or through another connection, for example through a remote server which tracks and stores all of the above and other status information and provides the above and other functions to such clients and customers.

Figure 31:
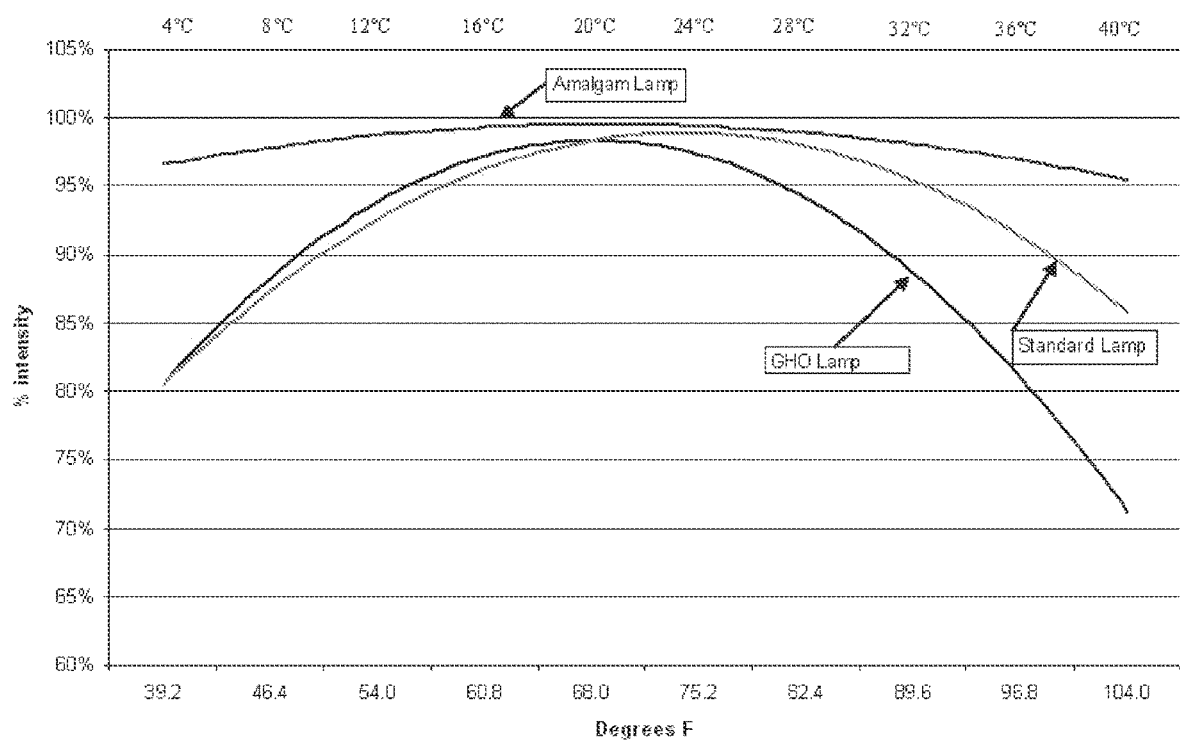
FIG. 31 is a graph depicting temperature stability comparisons of different lamps.

An advantage of ozone generation using UV lamps is that no static charge or residue is produced. Preferably the present invention uses a category of UV lamps known as amalgam lamps. Amalgam lamps contain no mercury and have benefits over other types of UV lamps, such as standard UV or germicidal (GHO) lamps, such as better stability, longer life and higher power output. The optimal operating temperature for air surrounding the lamps is 20 to 25° C. As reflected in FIG. 31, the performance of the amalgam lamps will decrease as the temperature of the air surrounding the lamps goes above or below 20 to 25° C. One skilled in the art would recognize, however, that the present invention is not limited to using amalgam lamps over other UV lamps.

While a preferred blower in the present invention has the capacity to move 100 cfm, the selection of a blower is not a limitation herein. When using a non-variable speed blower, a person skilled in the art could easily choose a blower with the appropriate capacity based on design specifications to meet specific ozone generation requirements, and to optimize performance. As indicated above, the concentration of ozone can be controlled by the volume of air pushed through the lamp housing assemblies containing UV lamps. In one embodiment, as the volume of air increases, the concentration of the ozone increases; and as the volume of air decreases, the concentration of the ozone decreases. In one embodiment, ambient air flow of approximately 35 cfm produces ozone at a concentration of about 79 ppm.

Similar to FIGS. 1-14, FIGS. 15-28 show a further embodiment of a portable ozone generator, only which utilizes a cylindrical or tubular lamp housing rather than the rectangular lamp housing depicted in FIGS. 1-14. FIGS. 15-28 show an exemplary embodiment of an ozone generator 38 that is a portable ozone generator unit having a housing 39 with a front end 46 and a rear end 41. The housing 39 has wheels 47a and 47b (not shown) attached to the rear end 41. The housing 39 also has a hinged lid 42 that can be kept securely closed by latches 43a and 43b. The hinged lid 42 has a circular opening 48 through the rear end 41 through which the ozone outlet 45 exits the housing 39. A cap 44 may be used to close circular opening 48 when the ozone generator is not in use. Cap 44 may be connected to housing 39 by a wire. Alternatively, circular opening 48 may be closed using an automatic shutter rather than cap 44. Housing 39 also has an extendable handle 51 on its front end 46 that allows ozone generator 38 to be moved by pulling ozone generator 58. Extendable handle 51 may have a grip 52 to make pulling the ozone generator 38 easier and more comfortable for the user. Although not shown in FIG. 15, a fixed handle may alternatively be used to move ozone generator 38.

Figure 15:
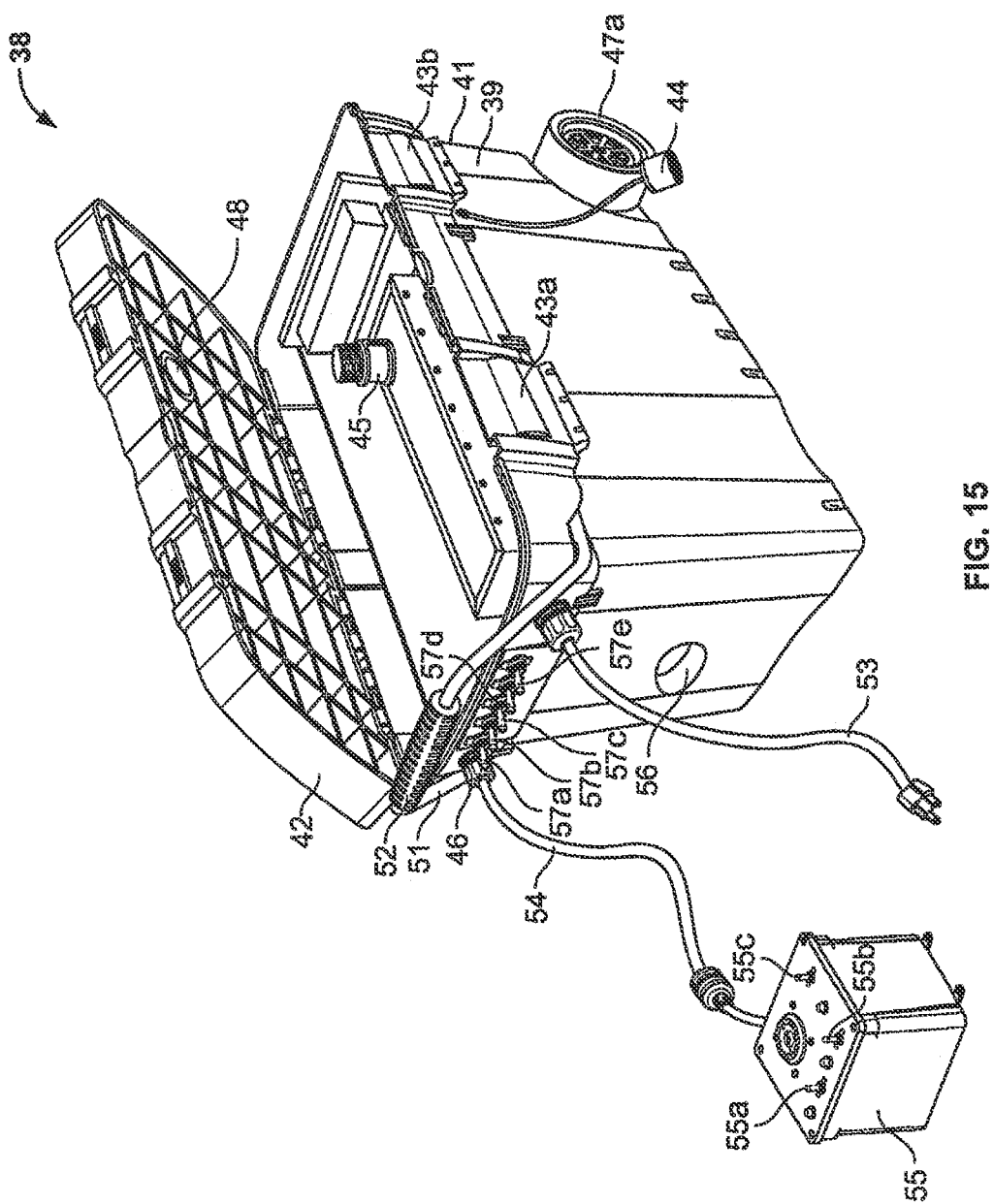
FIG. 15 is a front right perspective view of one embodiment of an ozone generator with an open lid.

FIG. 15 also shows a power cord 53 extending from front end 46. A cable connection 54 also extends from front end 46, and is used to connect a control unit 55 to the ozone generator 38. Power cord 53 and cable connection 54 are attached to housing 39 through respective openings in housing 38. Housing 38 also has an air inlet 56 on front end 46 to allow for the flow of air into ozone generator 38. Air inlet 56 is centrally located below extendable handle 51. In one embodiment, the air inlet 56 has a 2⅝ diameter. In a further embodiment, the control unit 55 has toggle switches 55a, 55b, and 55c. Toggle switch 55a turns the power of ozone generator 38 on and off. Toggle switch 55b turns a timer 74 on and off. Toggle switch 55c allows a user to override settings of timer 74. Timer 74 may be any type of timer, including mechanical and digital timers. For example, timer 74 may be a 24-hour mechanical timer that has 15 minute setting intervals that allow a user to operate ozone generator 1 at 15 minute intervals over a 24-hour period. In another embodiment, front end 46 has toggle switches 57a, 57b, 57c, 57d, and 57e that turn ultraviolet lamps within housing 39 on and off. The number of toggle switches can vary directly with the number of UV lamps used. One skilled in the art will be understand that other types of switches known in the art could be substituted for the toggle switches without altering the invention. Although FIG. 15 shows cable connection 54, it is contemplated that a wireless remote control unit can also be used to operate ozone generator 38, as described above. For example, in one embodiment, ozone generator can be operated using a remote control, so that the user is positioned outside of the enclosed space being treated and the user can operate the ozone generator safely from outside of the enclosed space being treated. The use of a wireless remote control unit is advantageous because it eliminates the need for cable connection 54.

Figure 16:
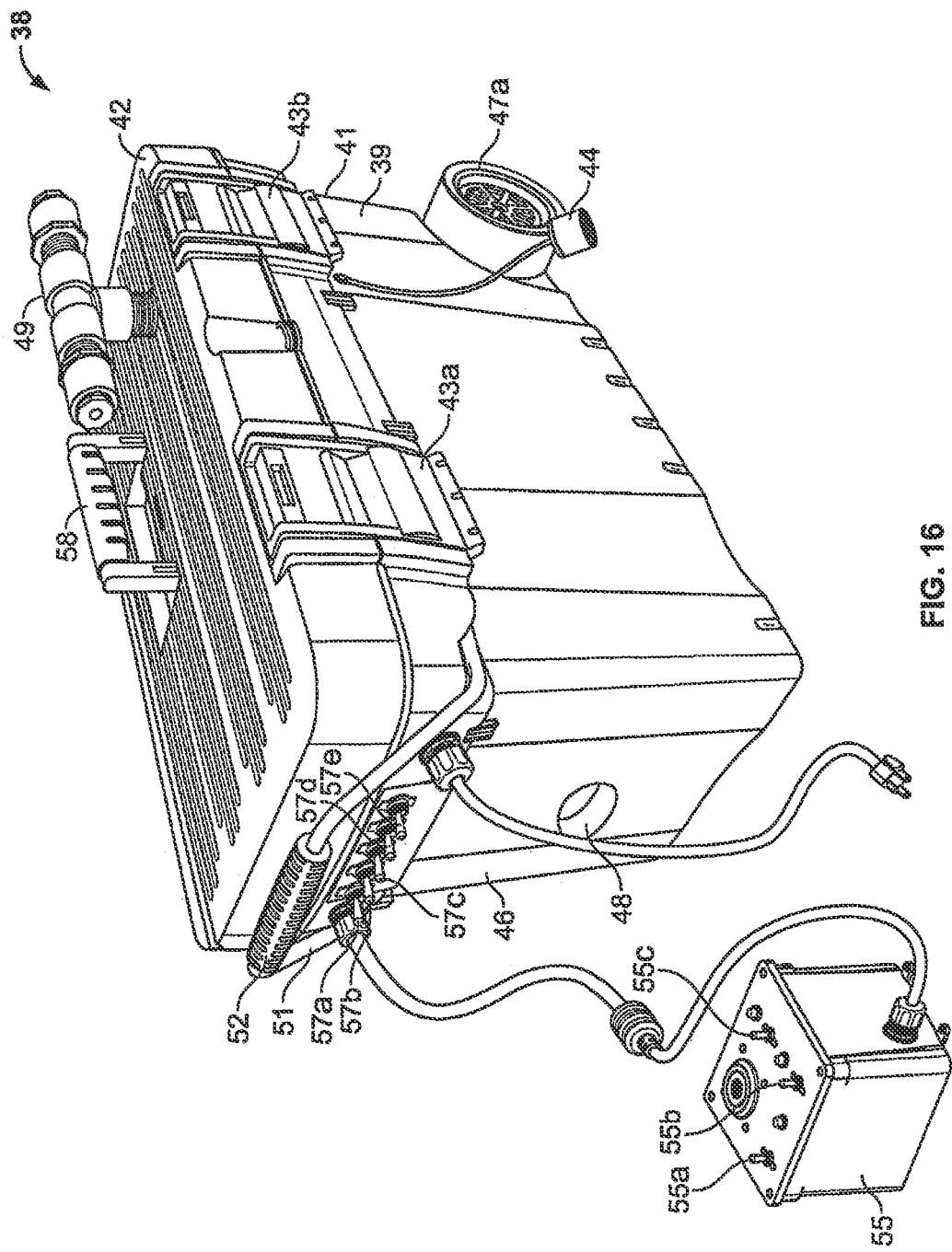
FIG. 16 is a front right perspective view of the ozone generator of FIG. 15 with a closed lid.

The ozone generator 38 of FIG. 16 includes all of the elements of the ozone generator 38 of FIG. 15 and shows the ozone generator 38 with the hinged lid 42 in a closed position. A diverter 49 may be screwed onto ozone exhaust outlet 45 to allow for the flow of ozone from inside the housing 39. The diverter 49 may be made from Schedule 80 piping. In an exemplary view, the hinged lid 42 has a handle 58 that provides for lifting ozone generator 38.

Figure 17:
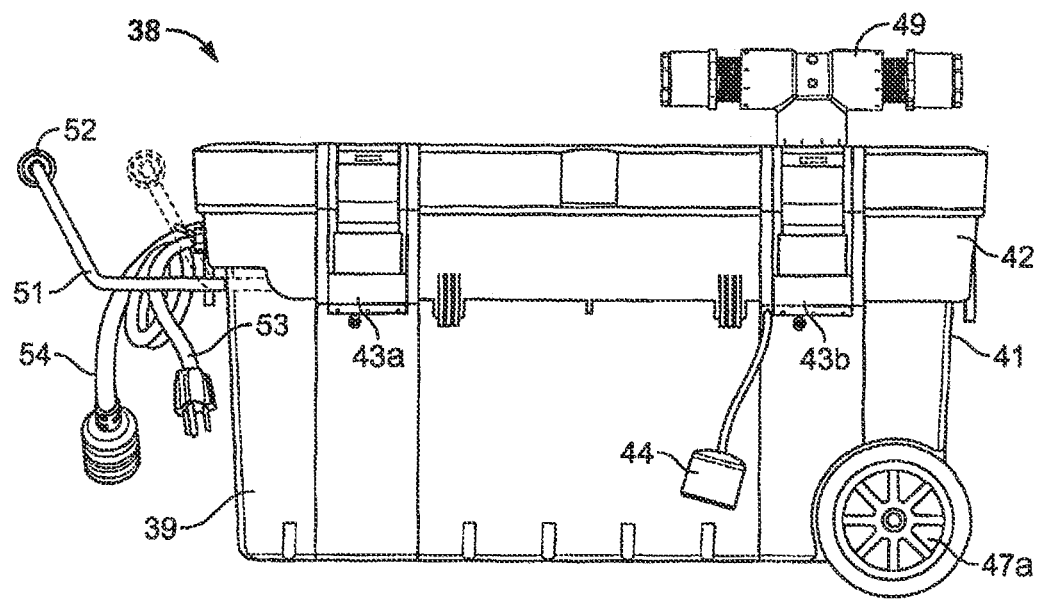
FIG. 17 is a right side elevation view of the generator of FIG. 16 without hose connections.

FIG. 17 provides a view of the right side of the ozone generator 38. The extendable function of extendable handle 51 is also illustrated in FIG. 17.

Figure 18:
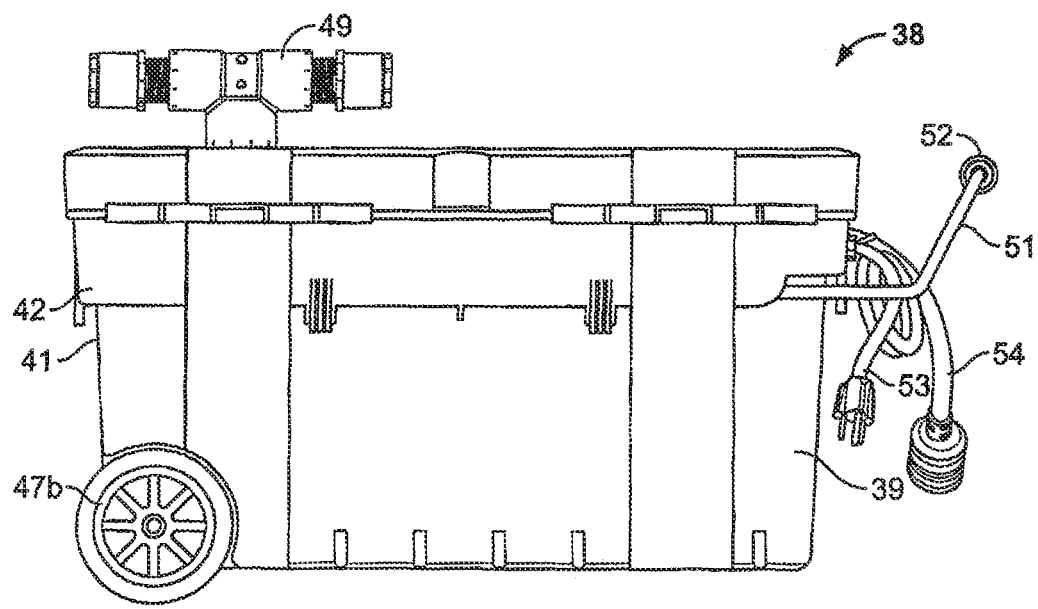
FIG. 18 is a left side elevation view of the generator of FIG. 16 without hose connections.

FIG. 18 provides a view of the left side of ozone generator 38. In one embodiment, housing 39 is approximately 22 inches long, 16 inches high, and 14 inches wide. One skilled in the art would easily recognize other sizes, shapes, and configurations are possible for the housing and the present invention is not limited to any specific sizes, shapes, configurations, or dimensions.

Figure 19:
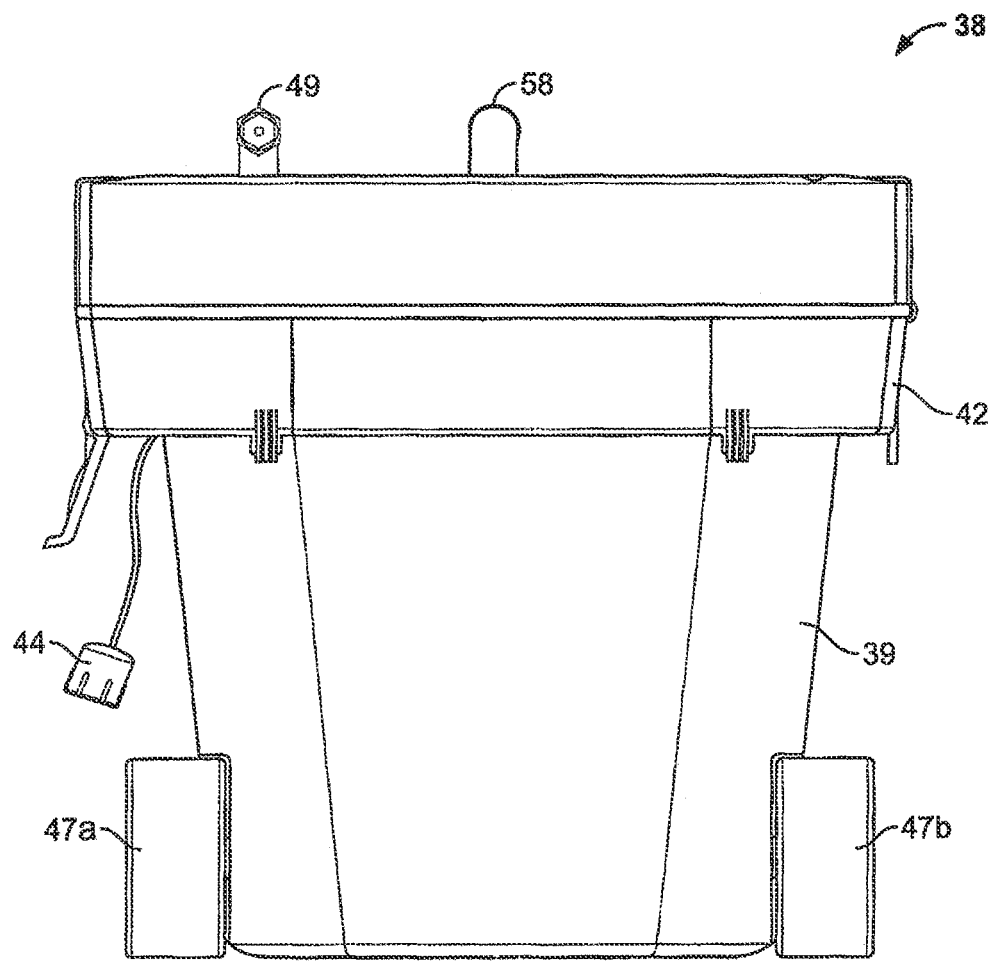
FIG. 19 is a rear elevation view of the generator of FIGS. 15 and 16.
Figure 20:
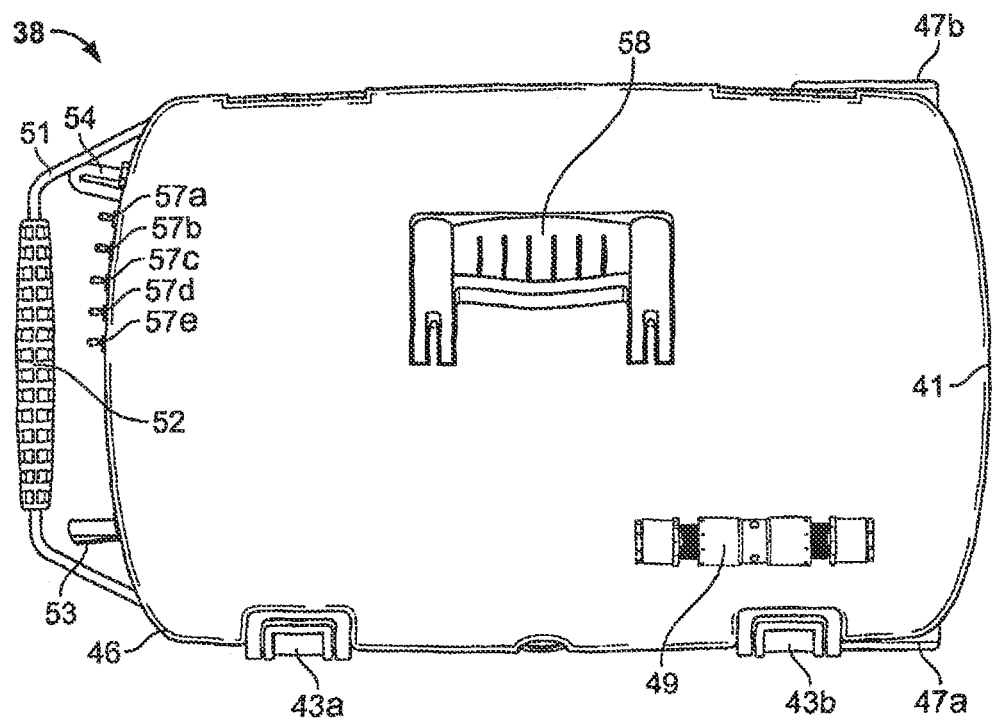
FIG. 20 is a top view of the generator of FIGS. 15 and 16.
Figure 21:
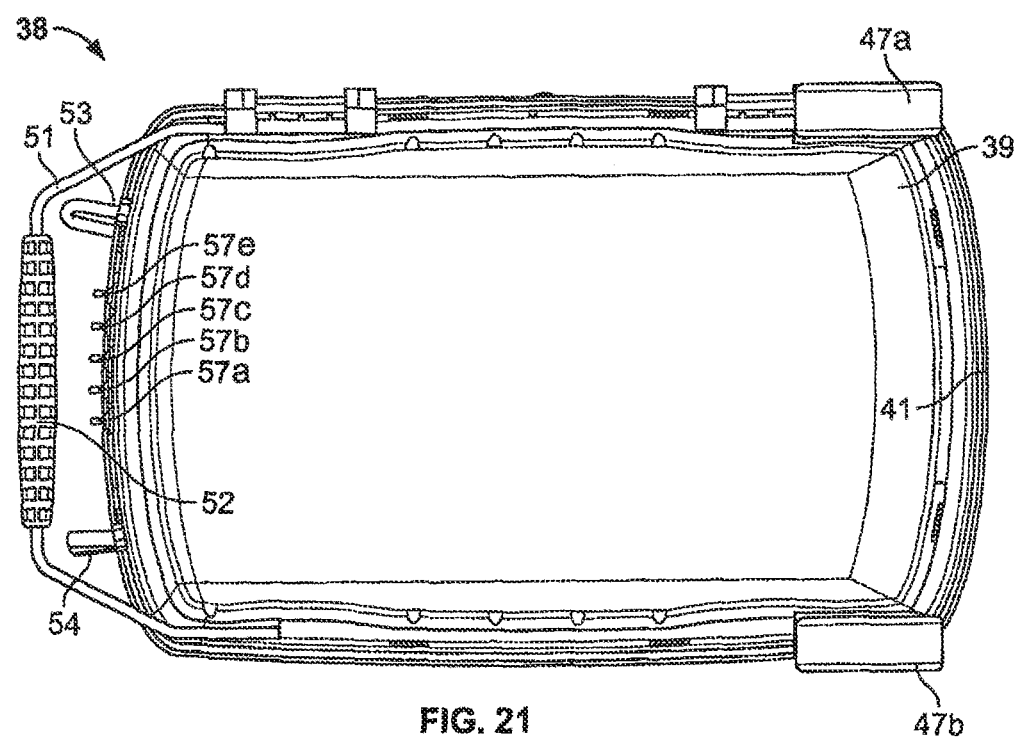
FIG. 21 is a bottom view of the generator of FIGS. 15 and 16.

FIG. 19 is a rear elevation view of generator 38 showing housing 39 and diverter 49 for outbound ozone. FIG. 20 is a top view of ozone generator 38 with handle 58 and diverter 49. FIG. 21 shows the bottom side of ozone generator 38.

Figure 22:
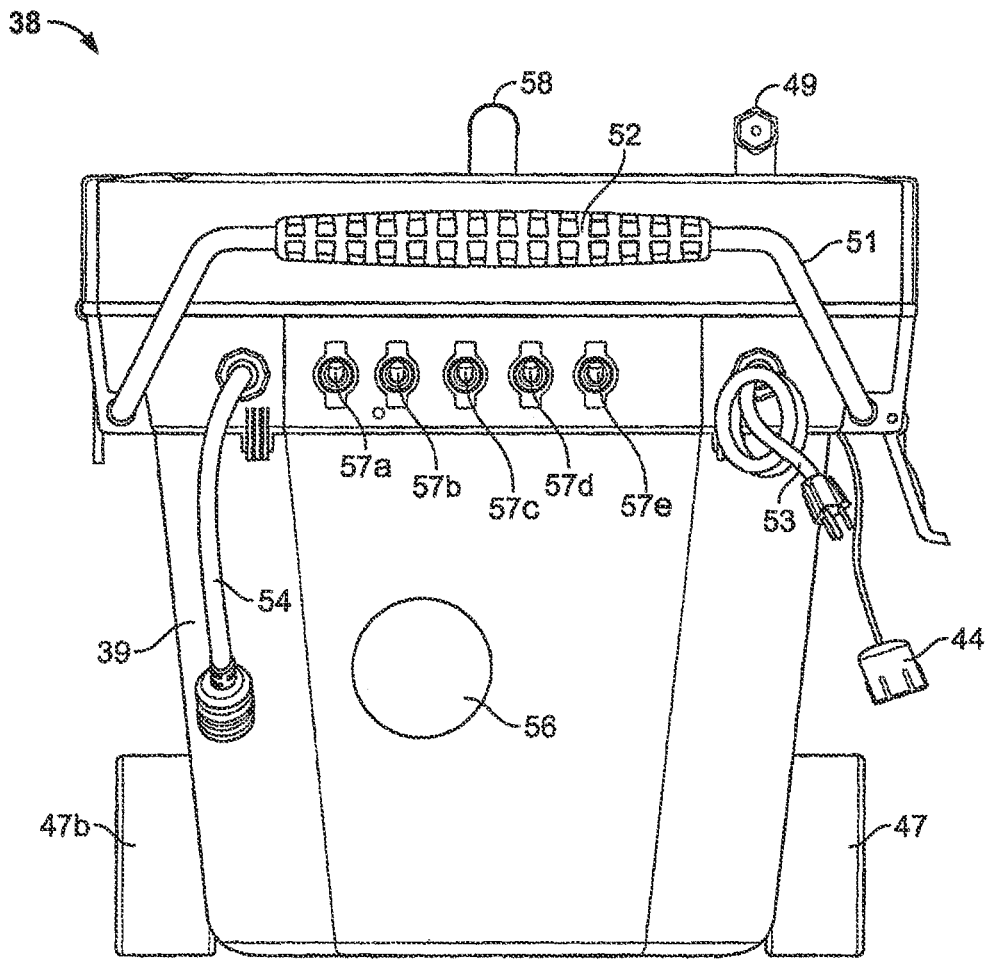
FIG. 22 is front elevation view of the generator of FIGS. 15 and 16.

FIG. 22 is a front elevation view of ozone generator 38 showing housing 39 with air inlet 56. In an exemplary embodiment, air inlet 56 is a circular orifice that is approximately 2⅝ inches in diameter. Air from the enclosed space to be treated enters air inlet 56, then proceeds to blower 67 (not shown) which causes air to enter lamp housing 60 (not shown). The air is converted to ozone gas by the set of ultraviolet lamps 61 (not shown) as it circulates around the ultraviolet lamps 61 in the lamp 60 housing. After ozone is created, it will exit via ozone outlet 64 to ozone exhaust outlet 45 to diverter 49, and then to outside ozone generator 38 into the space being treated.

Figure 23:
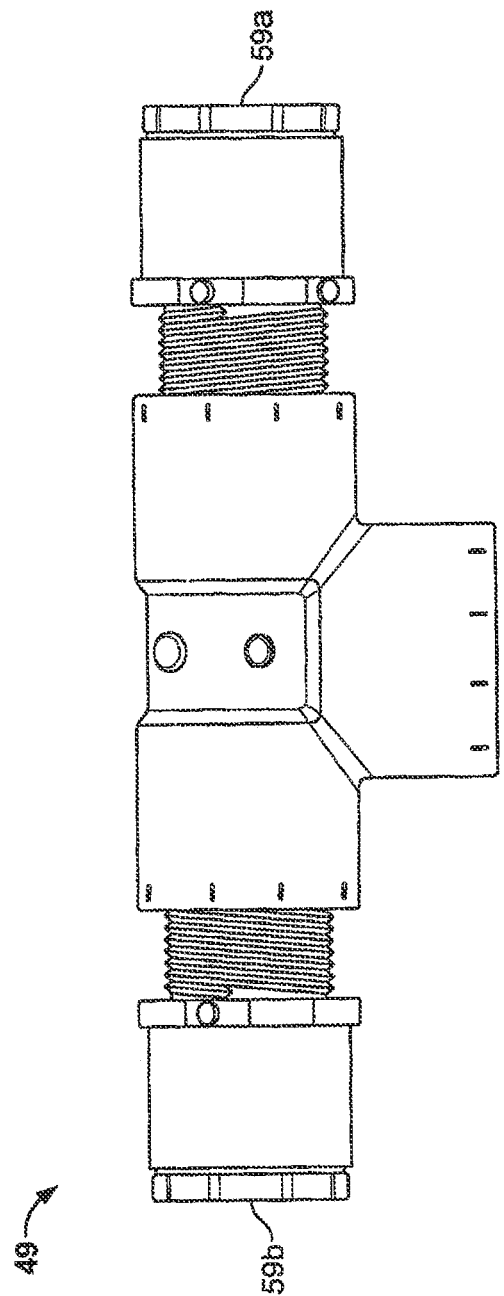
FIG. 23 is a front view of the diverter of FIG. 16.

FIG. 23 provides a front view of diverter 49 of FIG. 16. When using ozone generator 38, hinged lid 42 is closed and diverter 49 is screwed onto ozone exhaust outlet 45. Diverter 49 has ozone outlets 59a and 59b for exit of ozone from ozone generator 38. Ozone outlets 59a and 59b provide back pressure to prevent dissipation of ozone prior to exiting ozone generator 38, and to ensure that the ozone maintains the highest concentration possible. In one embodiment, the ozone outlets 59a and 59b have ⅜ inch diameters.

Figure 24:
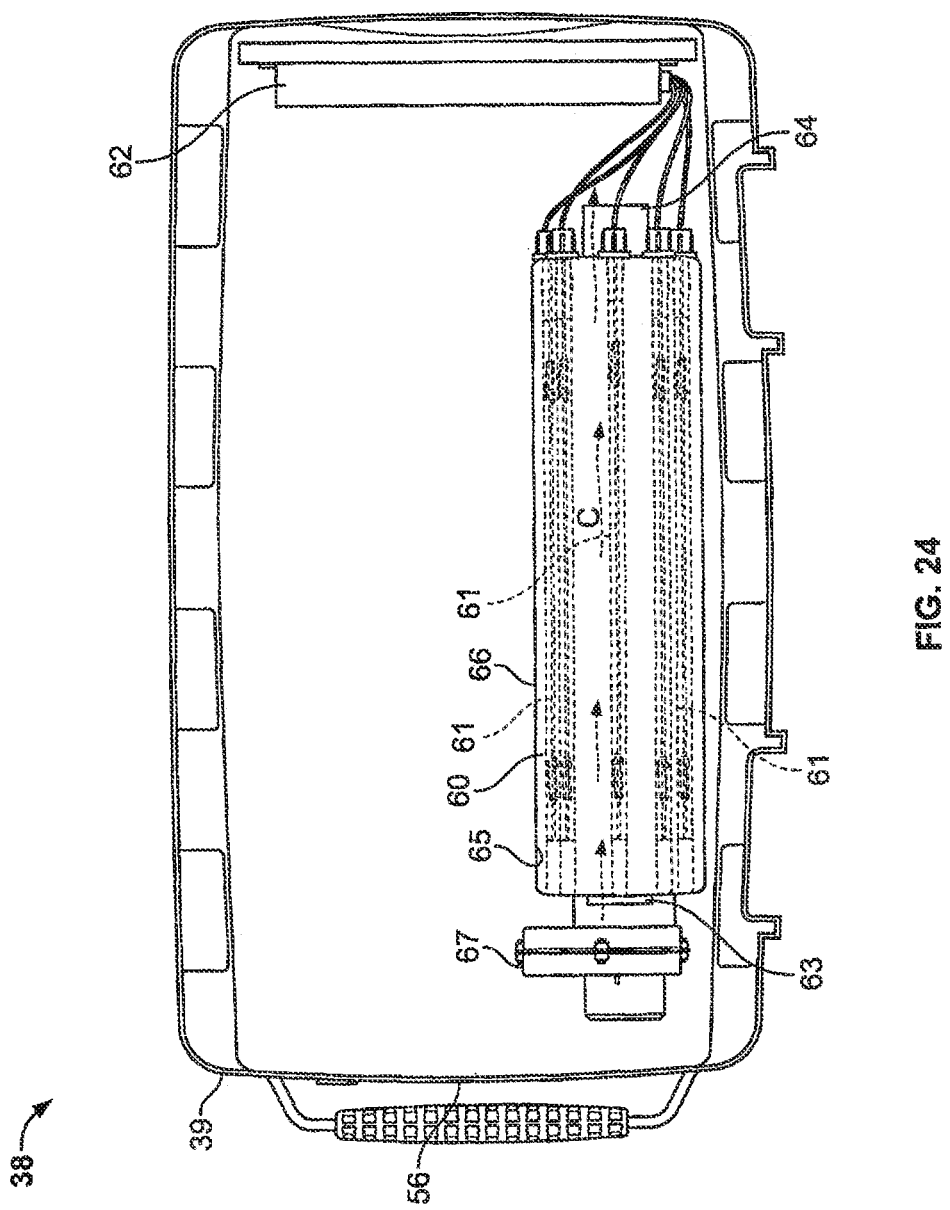
FIG. 24 is a top view of one embodiment of an ultraviolet lamp housing.

FIG. 24 is a top view of one UV lamp housing 60. The lamp housing 60 shown is cylindrical and has an air inlet 63 and an ozone outlet 64. The air inlet 63 and the ozone outlet 64 in the lamp housing 60 of FIG. 24 are positioned at the center of each side of the lamp housing 60. Preferably, in one embodiment, the air inlet 63 is 2⅝ inches in diameter, and the ozone outlet 64 is 1 inch in diameter. However, the diameters of the air inlet and ozone outlet will vary depending on the size of UV lamp housing, the type of blower ballasts and the number of UV lamps within the UV lamp housing, among other possible variables. In operation, air enters the air inlet 63 and generally flows down or along the center of the lamp housing 60, generally along path indicated by line C shown in FIG. 24. After the air, or components thereof, is converted to ozone, the ozone will exit lamp housing at ozone outlet 64. Path C is generally representative of the flow of air entering and ozone exiting the housing. In one embodiment, a fan or blower 67 is placed proximate the air inlet 63 for forcing or causing the air to move along the line or path C. The blower 67 pulls outside air into ozone generator 38 through air inlet 56. Although the air generally moves in the direction of path C, the blower 67 causes air to circulate in various directions within the UV lamp housing for improved air circulation around the UV lamps as air flows down or along the lamp housing 60 to ozone outlet 64.

The UV lamp housing 60 shown in FIG. 24 has an inner surface 65, and an outer surface 66. In one embodiment, the distance between inner surface and outer surface is ⅜ inches. The UV lamp housing 60 can have a casing made from a polymer that surrounds UV lamps 61. In one embodiment, the polymer is a polypropylene in sheet form. The UV lamp housing 60 can house between 1 and 20 UV lamps, depending at least on the diameter of the UV lamp housing 60 and the size of the UV lamps, but more lamps may be used. In one embodiment, the lamp housing 60 has a diameter of 12 inches. As indicated, the number of UV lamps used within the lamp housing 60 and ozone generator 38 may vary. When viewed from a top view, the lamp ballasts 62 shown in FIG. 24 are connected to the rear end of lamp housing 60 for each UV lamp. The lamp ballasts provide power for the UV lamps contained within the lamp housing 60 via connectors, similar to prior embodiments described herein, such as the embodiment shown in FIG. 10.

Figure 30:
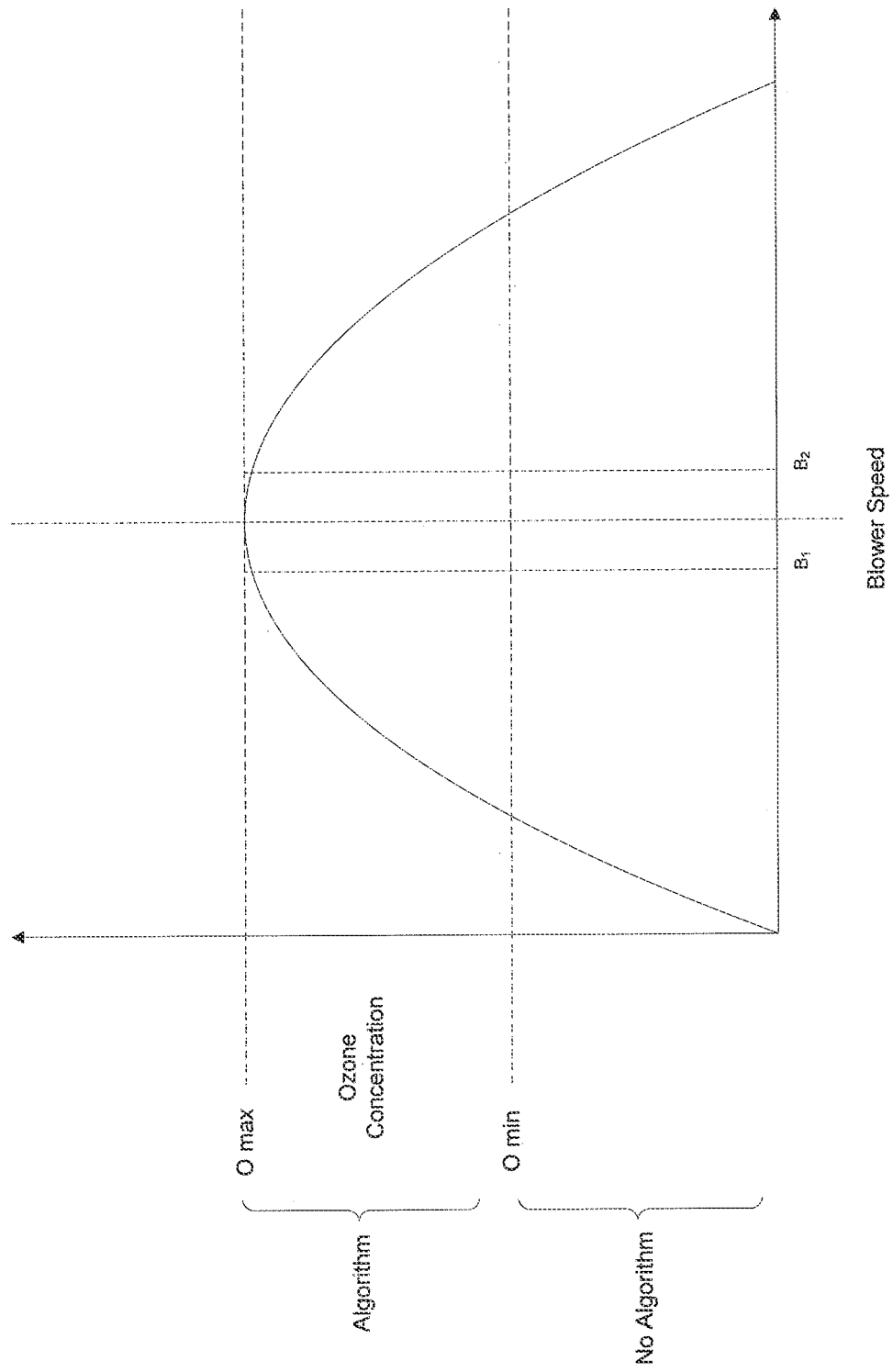
FIG. 30 is a graph depicting ozone concentration vs. blower fan speed for optimizing the ozone concentration.

As in prior embodiments of ozone generator 1 depicted in FIGS. 1-14, the lamp ballasts of FIG. 24 regulate the flow of power through the UV lamps. One lamp ballast is used per ultraviolet lamp that is housed within lamp housing. Lamp ballasts may also be placed outside the housing 39. In one embodiment, the optimal ambient temperature of air entering the lamp housing 60 and proximate the ballasts is 20 to 25° C. Air exceeding 40° C. may prevent maximum or optimal conversion of air or components thereof into ozone. As such, switches can be used in connection with (and can be connected to) the lamp ballasts to allow the ozone generator's user to turn off the lamp ballasts when the operating temperature range exceeds the operating temperature range. This feature of the invention helps to prevent damage to the ozone generator. In a further embodiment, instead of or in addition to these manual switches, the ozone generator 38 can include automatic switching thermal switches connected to the lamp ballasts between the power source and each ballasts for shutting off power to each ballast when the temperature exceeds the operating temperature range. Alternatively, these switches can be connected to the controller shown on FIG. 30. A temperature sensor (input) can be connected to the controller for transmitting a temperature signal to the controller. The controller can then determine whether the received temperature signal indicates that the temperature is greater than a predetermined temperature. If the temperature is greater than the predetermined temperature, then the controller can send a signal to one or more of the switches for toggling one or more of the switches to shutting off or cutting off power to one or more of the ballasts, for preventing damage to the ozone generator and/or reducing hazards which could end up causing a fire.

Figure 25:
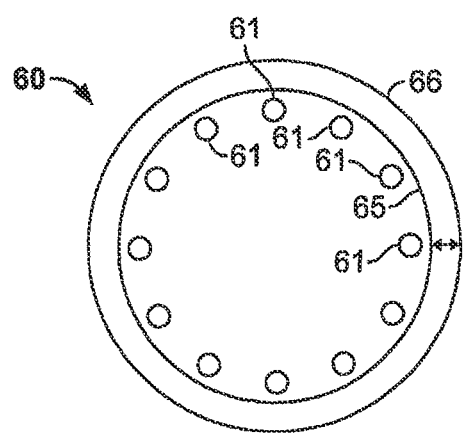
FIG. 25 is a cross-sectional side elevation view of the housing of FIG. 24 having twelve UV bulbs.

FIG. 25 is a cross-sectional front view of lamp housing 60 of FIG. 24. In an exemplary embodiment, a set of twelve ultraviolet lamps 61, each of which emits UV radiation, is positioned equidistant around the inner surface 65 of the lamp housing 60. In one embodiment, the spacing of the UV lamps about the inner circumference of the inner surface 65 is such that there is at least one inch between the inner surface 65 and each UV lamp, and such that there is at least two inches between each ultraviolet lamp to ensure optimal air circulation around and about each UV lamp. Preferably, the distance between each UV lamp ranges from 2 to 2.5 inches, and the distance between each UV lamp and the inner surface 65 ranges from 1 to 2 inches. Air enters air inlet 63 and flows around and about the UV lamps prior to exiting the lamp housing 60 from ozone outlet 64. The air is thus exposed to radiation from the UV lamps to allow the oxygen in the air to be converted to ozone as a result of the air's exposure to the UV lamps. In one embodiment, the space between each individual UV lamp 61 is at least two inches. Although not shown in FIG. 25, each UV lamp has lamp connectors that attach the ultraviolet lamps 61 to the lamp ballasts 62 of FIG. 24.

Figure 26:
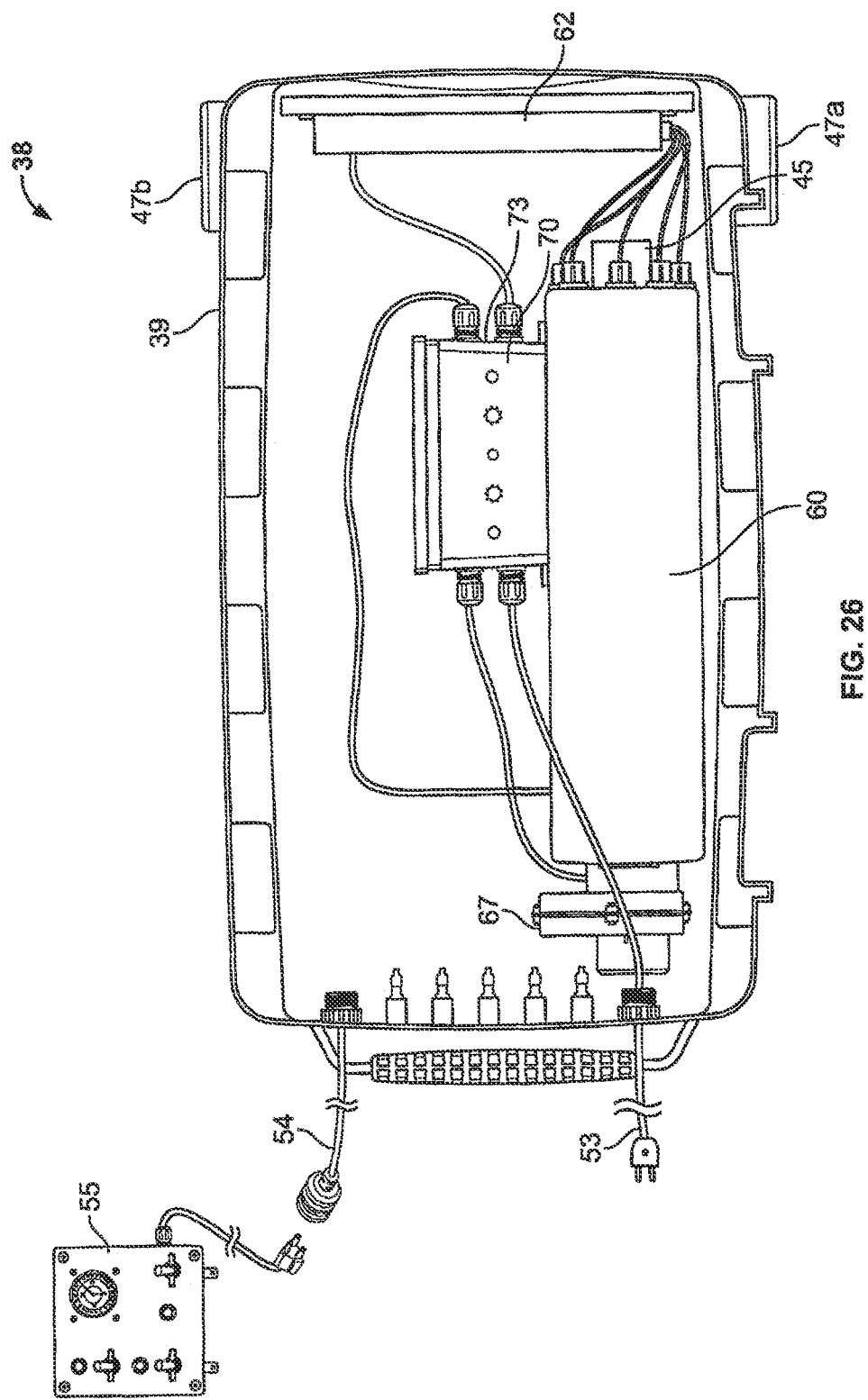
FIG. 26 is a top view of the generator of FIG. 15 with the lid off, showing interior details.

FIG. 26 shows the interior detail of the components of the ozone generator 38 with hinged lid 42 removed. The blower 67 therein pulls or creates a force that sucks air into ozone generator 38 through air inlet 56. An exemplary blower is one that is quiet and capable of moving 100 cubic feet of air per minute (100 cfm). One skilled in the art would recognize that the type of blower used can vary based on at least the size of the ozone generator and number of lamps used. Similar to the embodiments in FIGS. 1-14, a wiring box is positioned in the housing, and can be positioned behind blower unit 67, and can contain a connector for an auxiliary lamp housing assembly, a connection for cable connection 54 and power cord 53, a second connector for lamp ballast 62, and third connector for lamp housing 60. The latch side of housing 39 contains UV lamp housing 60, and the wheel side of housing 39 contains lamp ballast 62. The ozone generator 38 can also have a set of baffles positioned at the entrance to the UV lamp housing (either just outside of or just inside of the lamp housing) to force the air coming into contact with the baffles to disperse, in order to improve air circulation within the UV lamp housing, which may also assist in preventing the ozone generator from overheating. Various shapes of baffles can be used, including, for example, fan shaped baffles, propeller shaped baffles, winged shaped baffles, shutter shaped baffles, and other shaped baffles.

Figure 27:
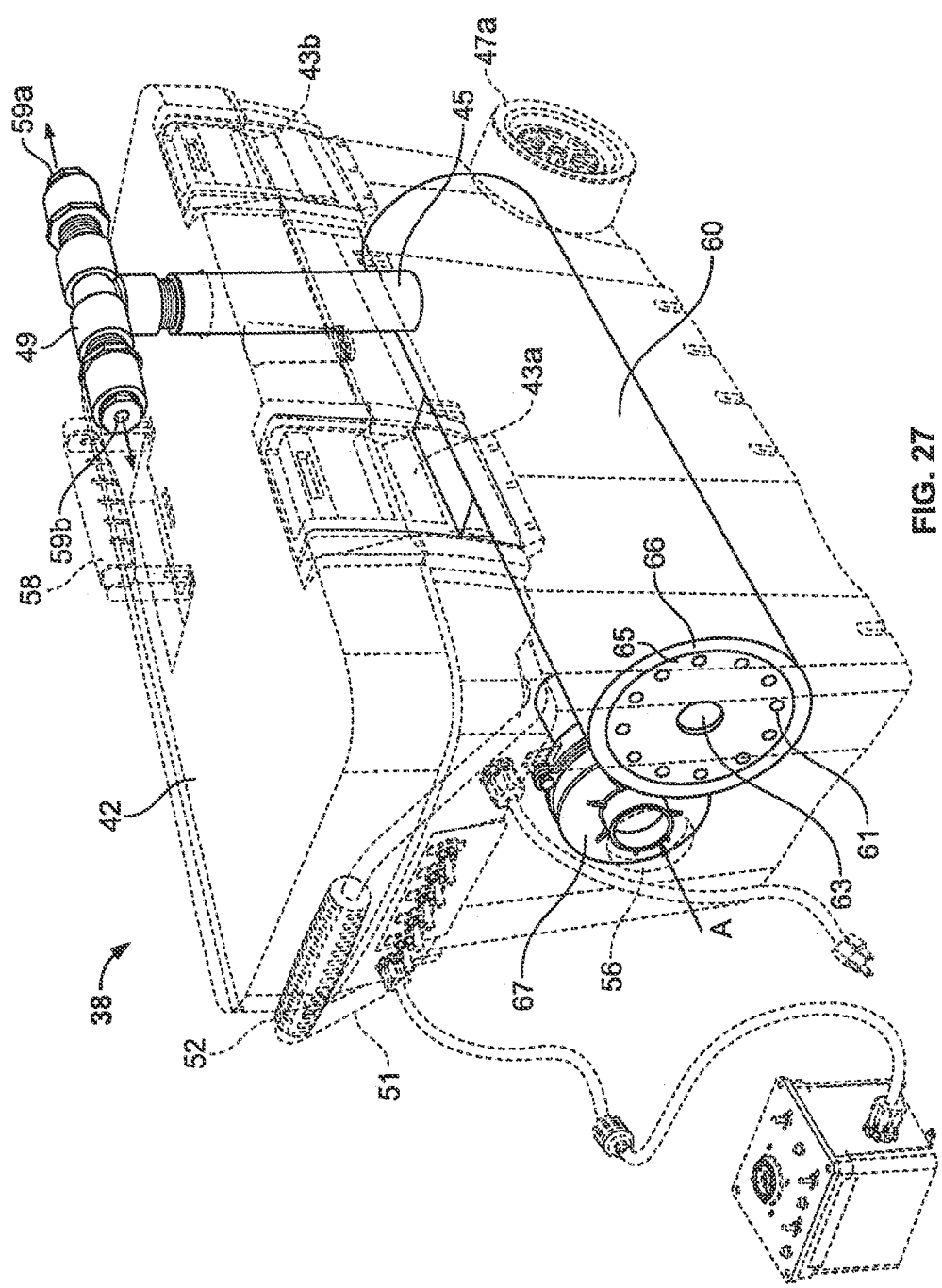
FIG. 27 is a front right perspective view of the generator of FIG. 16 with the phantomed housing.

FIG. 27 is a front right perspective view of ozone generator 38 with the housing 39 phantomed. At the front, air inlet 56 connects to blower unit 67. Air flowing into ozone generator 38 is represented by arrow A. The air flows at a rate that varies with the size of the ozone generator, so that a larger ozone generator will have a higher flow rate. In one embodiment, when ozone generator 38 is operating, air flows through lamp housing 60 where the ozone gas is produced at concentrations of at least 75 ppm. When diverter 49 is screwed onto ozone outlet 45 to connect diverter 49 to lamp housing 60 during ozone generator operation, air having increased ozone content is released through ozone outlets 59a and 59b.

Figure 28:
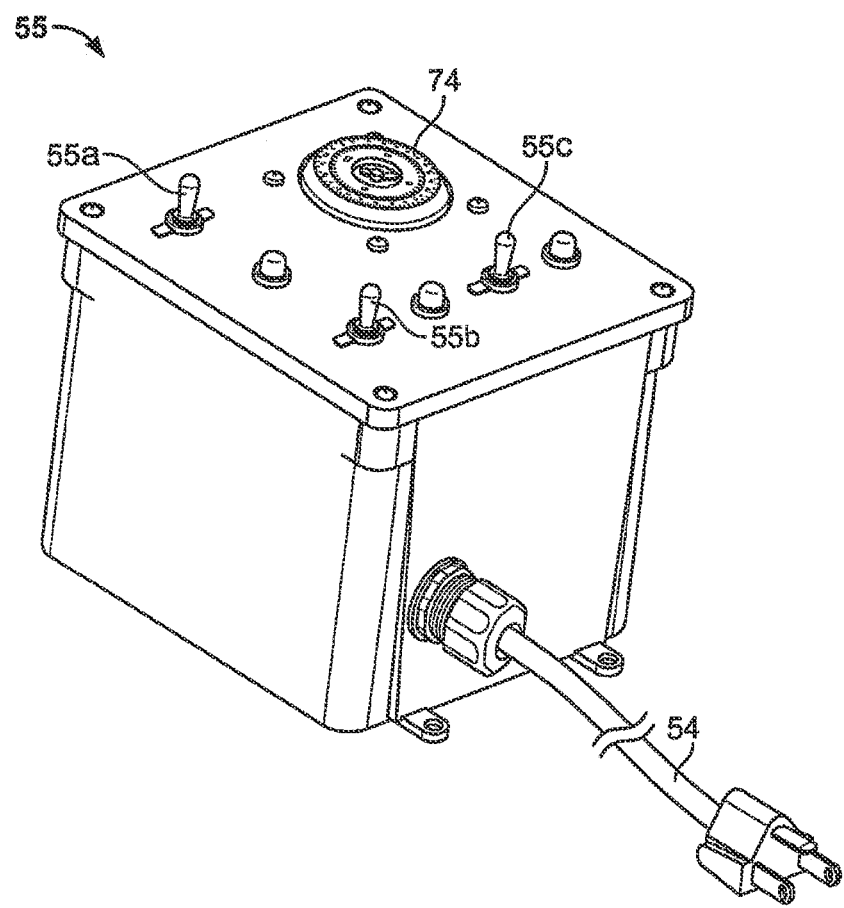
FIG. 28 is an enlarged perspective drawing of one embodiment of a timer/controller unit.

The control unit 55 shown in FIG. 28 can be used to remotely control the operation of ozone generator 38 by directly switching on or off blower 67, UV lamps 61, or other components, as desired. For example, FIG. 28 shows the control unit 55 configured with a timer 74 that can be set for starting and stopping the operation of ozone generator 38 from a remote location. Each of three toggle switches 55a, 55b, 55c corresponds to an electrical connection in wiring box 70 and is positioned proximate to a light which indicates when the switch is turned on or off. In one example, first toggle switch 55a turns on blower 67, second toggle switch 55b controls ultraviolet lamps 61, and third toggle switch 55c controls timer 74. Cable connector 54 is used to connect control unit 55 to ozone generator 38. Depending on the distance from the user's location and the ozone generator, the cable connector's length may vary. For example, the cable connector may be 50 feet in length. One of skill in the art can better understand the structure and operation of the present control unit and with reference to the control unit of the previously described embodiments herein, as well the respective portions of the ozone generator.

The UV lamp housing, in rectangular, cylindrical or other shaped embodiments, may be single modular units that can be easily removed and replaced. This feature allows users to replace the UV lamp housing without replacing the entire unit. As such, in order to replace the UV lamps on a periodic basis, in one embodiment of the present invention, the following configuration and method can be utilized. When a user or other individual opens the lid of the ozone generator, such individual can gain access to the UV lamp housing. In one embodiment, the UV lamp housing can be connected to a power source and/or ballasts through a single connection, which can be a plug or other releasably attachable connection from the power source/ballasts to the UV lamp housing and UV lamps therein. This releasably attachable connection can have separate leads running from each ballast to each of the UV lamps within the UV lamp housing, such that all connections from the ballasts to the UV lamps can be connected and disconnected from the one releaseably attachable connection. This one connection allows for ease of removal of the UV lamp housing. In addition, the UV lamp housing can be connected to the interior of the ozone generator housing using a releasably attachable clamp or other means for releasably attaching the UV lamp housing to the ozone generator housing. Mechanisms similar to base stations for laptop computers can be utilized for releasably attaching the UV lamp housing to the ozone generator housing, which can use a lever to release and/or secure moveable arms our of and into grooves, notches, slots and/or other openings within he UV lamp housing. The arms can engage the grooves, notches, slots and/or other openings when the lever is not extended, and disengage the grooves, notches, slots and/or other openings when the lever is extended or pulled. This is one example of how the UV lamp housing can easily be configured for engagement and disengagement from the ozone generator housing. Thus, in one embodiment, in order to remove the UV lamp housing from the ozone generator to replace the UV lamps or perform some other maintenance activity, the user need only open the lip to obtain access to the UV lamp housing, disconnect the single connector for electrical disengagement of the UV lamp housing from the ozone generator, and pull the lever, which will disengage one or more arms from the one or more grooves, notches, slots and/or other openings, for physical disengagement of the UV lamp housing from the ozone generator housing. The opposite can be performed to install a new UV lamp housing having new preloaded UV lamps therein. In an alternative embodiment, a separate releasably attachable connector can be used between each ballast and the UV lamp housing for each UV lamp therein to connect and disconnect the UV lamp housing from the ozone generator, to more easily replace the UV lamps by replacing the UV lamp housing all at once.

In one embodiment, the present invention is directed to a method of replacing UV lamps within an ozone generator. Instead of replacing UV lamps individually or providing UV lamps to users of ozone generators to replace UV lamps one at a time, an ozone generator manufacturer or distributor can distribute UV lamp housings, which match previously distributed UV lamp housings within previously distributed ozone generators, having preloaded new UV lamps therein. Once received by the users of the ozone generators, the UV lamp housings with preloaded new UV lamps therein can be used to replace the old or used UV lamp housings and old or used UV lamps therein, in order to service the ozone generators in a more efficient manner. Once the UV lamp housings are received with the new UV lamps therein, the user, as indicated above, can open the lid of the ozone generator to access the old or used UV lamp housing, which houses the old UV lamps. The user can then disconnected the electrical and physical connections, and connect the received UV lamp housing with the new UV lamps therein, to more efficiently replace the UV lamps, as described herein. In one embodiment, the user is provided an incentive, such as a reduced price for the new UV lamp housing, a rebate for the old UV lamp housing, or compliance with a service contract, or some other incentive to return the old UV lamp housing to the manufacturer or distributor of the UV lamp housing. Shipping costs can be paid by the manufacturer or distributor as a part of the incentive. In another embodiment, as a part of a service contract or otherwise, the manufacturer or distributor can send service personnel to where the ozone generator is located to replace the UV lamp housing and UV lamps therein according to the method of replacing the UV lamp housing and UV lamps therein described herein. In either embodiments, the manufacturer or distributor can efurbish the UV lamp housing by replacing the UV lamps, checking the electrical connections, replacing any electrical connections that may need replacing and possibly even verifying air flow and ozone generation performance of the refurbished UV lamp housing prior to redistributing the refurbished UV lamp housing.

As described herein, the first described ozone generator 1, as well as the other ozone generator 38 described herein, in a similar fashion as the first described ozone generator 1 herein, may use a controller, such as the controller shown and described in FIG. 29, in a similar fashion to optimize the ozone generated by the ozone generator. Further referring to FIG. 29, a further embodiment of the ozone generator 3000, similar to previously described ozone generators herein, is provided in which the ozone generator 3000 optimizes the production of ozone by using closed-loop control. As previously described, use of a controller 3002 having an control application 3006 that utilizes closed-loop control ensures optimal ozone is generated by the ozone generator 3000 by factoring out variations in ozone generation that can be caused by change in temperature, sizes of inlets and outlets, lamp intensity, humidity and other factors. The ozone generator 3000 is similar to the ozone generators disclosed in the previously described embodiments of the present invention as depicted in FIGS. 1 to 29 in that it comprises a portable housing with an air inlet and an ozone outlet, an ultraviolet housing with an air inlet and an ozone outlet, a set of ballasts, and a control unit with a timer for operating the generator, among other components and elements. In one embodiment, the controller 3002 and the control application 3006 therein is programmed to not turn on the closed-loop control until after completion of a warm up period. In one embodiment, the warm up period corresponds to the amount of time between when power for ozone generator is turned on and when the set of UV lamps have reached maximum intensity. One way to measure when this warm up period has ended is to utilize a temperature sensor to measure lamp temperature 3040. The controller 3002 and the control application 3006 therein can compare the measured temperature with a predetermined steady state lamp temperature and determine if the predetermined steady state lamp temperature has been met. If yes, the UV lamps can be considered to have reached the maximum or steady state temperature, and the closed loop control can then be started. Other methods, such as determining when the rate of change of the measured temperature is zero or close to zero, can be used to conclude that the UV lamps have reach the maximum or steady state temperature, for determining when to begin closed loop control.

As previously described, in one embodiment, the controller 3002 and the control application 3006 therein can include a set point, one or more input signals one or more output signals, in a feedback loop arrangement. The controller 3002 and control application 3006 therein receives an input signal that corresponds to a concentration of ozone 3014 leaving ozone generator from ozone outlet. The concentration of ozone leaving ozone generator 100 is measured using a meter or sensor, which in one embodiment should be able to accurately measure the concentration of ozone in parts per million at high concentrations without sustaining damage as a result of exposure to ozone. The meter is placed proximate or next to the ozone outlet so that the concentration of ozone that exits ozone outlet can be determined. The concentration of ozone exiting ozone outlet corresponds to the concentration of ozone 3014 that ozone generator is producing at the time of measurement. The meter or sensor generates an input signal, which is transmitted to the controller 3002. As preciously described, the controller 3002 and control application therein 3006 runs an algorithm to compare the input signal to the set point. The algorithm can be configured to optimize the concentration of ozone in relation to outputs, such as the speed of a variable speed blower 3008, as previously described, to ensure that the concentration of ozone produced by the ozone generator exceeds a minimal threshold as reflected in FIG. 30. Continuing with additional reference to FIG. 30, the actual operating speed of blower or air speed 3030 is sent as a feedback signal to the controller 3002, so that the speed of blower 3008 may be adjusted depending on the concentration of ozone 3014 being produced. An output signal is then generated that depends on the difference between the set point and the input signal and the feedback signal. In one embodiment, optimal ozone concentration 3014 is produced when the set point and input signal are equal and blower is running at speeds between B1 and B2, shown in FIG. 30. When the controller 3002 and control application 3006 therein are operating, maximum concentration of ozone will be produced at speeds between B1 and B2.

In one embodiment, variable speed blower blows the air entering ozone generator towards the set of UV lamps so that the air may be exposed to the radiation being emitted from the set of UV lamps. The variable speed blower has an adjustable speed 3008 which depends on the output signal from the controller 3002. The output signal will cause the adjustable speed 3008 to increase or decrease depending on the concentration of ozone that is being produced by ozone generator 3000. The controller will use the feedback input signal (the ozone concentration 3014 and/or other inputs) and continue to transmit an output signal telling the variable speed blower to adjust the fan speed 3008 until it reaches the optimal speed (between B1 and B2 as shown on FIG. 30) to produce maximum concentration of ozone, as described herein.

According to one embodiment, the ozone generator 1 includes a plurality of UV lamp housings 20 (not shown), each UV lamp housing 20 including a plurality of UV lamps 27. For example, the ozone generator can include a second UV lamp housing 20 that is in series with, or parallel to, a first UV lamp housing 20. In such embodiments, the ozone generator 1 can include a second set of lamp ballasts 21, a second air inlet 22, a second ozone outlet 23, and/or a second diverter 16, so as to increase the utility and efficiency of the ozone generator 1. According to one embodiment, the air inlet(s) 22 and/or ozone outlet(s) 23 may be placed in various locations around the housing 2. For example, the air inlet(s) 22 could be placed on an opposite side of the housing 2 than the ozone outlet(s) 23.

According to one embodiment, the ozone generator 1 further includes mounting bumpers (not shown) adjacent to each UV lamp housing for securing the UV lamp housing and protecting it from unnecessary movement or jarring forces that could shorten the life of the UV lamps within. According to one embodiment, the ozone generator 1 further includes an air filter (not shown) to remove particulates from ambient air. According to one embodiment, the ozone generator 1 further includes a shut-off valve (not shown) adjacent to the ozone outlet 23. The shut-off valve may include a handle for manually opening or closing the valve.

A user can implement the following method of operating an ozone generator with any of the embodiments of the ozone generator disclosed herein. First, the respective ozone generator is put in a place where the air is to be treated. The person should put the ozone generator that consists of a portable housing with an air inlet and an ozone outlet, an UV housing that fits inside the portable housing, wherein the ultraviolet housing contains a set of ultraviolet lamps that emit ultraviolet radiation, a blower that is located within the portable housing, and a control unit with a timer that is connected to the housing for operating the ozone generator, inside the place to be treated. The place may be any room in a house, building, or sealable structure. The person then should exit the place to be treated, and confirm that the place to be treated is unoccupied and enclosed. After making this determination, the person can turn the ozone generator on using the control unit from outside of the enclosed place. The user can set the timer to run the ozone generator for desired periods of time. For example, the operator may set the timer to run for 15 minute intervals over a 24-hour period. The user can then leave the ozone generator to run for a sufficient amount of time that will allow for sufficient release of ozone into the place for treatment. The time for treating a place will vary depend on the concentration of ozone being released, the rate of flow of ozone into the place, and the size of the place that is being treated. After the ozone generator has been left on for a sufficient amount of time, the ozone generator may be turned off using the control unit or automatically set off by the timer.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the present invention and protected by the following claims.

What is claimed is:

1. An ozone generator comprising:
   a portable housing including a first air inlet and a first ozone outlet;
   a UV lamp section comprising UV lamps that are configured to emit UV radiation for generating ozone by applying UV radiation to air as the air moves through the UV lamp section;
   a blower contained within the portable housing to move the air into contact with the radiation of the UV lamps;
   a temperature sensor proximate to UV lamps to collect a temperature measurement of the air proximate to the UV lamps;
   a first output device configured to adjust an intensity of the UV lamps;
   a controller including a control application for execution within the controller, the controller and the application are configured to receive the temperature measurement from the temperature sensor and utilize a predetermined algorithm to control the first output device for adjusting the intensity of the UV lamps based on the temperature measurement;
   an ozone sensor proximate to the first ozone outlet to collect an ozone concentration measurement of the ozone exiting the first ozone outlet of the portable housing; and,
   a second output device configured to adjust at least one of an inlet size of the first air inlet and an outlet size of the first ozone outlet; wherein the controller and the application are configured to receive the ozone concentration measurement from the ozone sensor and utilize a predetermined algorithm to control the second output device for adjusting at least one of the inlet size and the outlet size based on the ozone concentration measurement.

2. The ozone generator of claim 1, wherein the controller and the application are configured to receive the ozone measurement from the ozone sensor and control the first output device further based on the ozone measurement.

3. The ozone generator of claim 1, further comprising an air sensor proximate to at least one of the first air inlet and the first ozone outlet to collect an air measurement of the air proximate to the at least one of the first air inlet and the first ozone outlet, wherein the controller and the application are configured to receive the air measurement from the air sensor and control the first output device further based on the air measurement.

4. The ozone generator of claim 1, wherein the first ozone outlet is an enhanced ozone air outlet, the first air inlet having a first diameter and the enhanced ozone air outlet having a second diameter, wherein the first diameter is greater than the second diameter.

5. The ozone generator of claim 1, wherein the plurality of UV lamps extend from a first end of the lamp section to a second end of the lamp section in a generally parallel configuration, the plurality of UV lamps comprising a first UV lamp and a second UV lamp, the first UV lamp being positioned adjacent a first side of the lamp section and the second UV lamp being positioned adjacent a second side of the lamp section, wherein the air enters the lamp section closer to the first side than the first UV lamp is positioned relative to the first side;
   wherein the blower has an operating speed; and
   a control unit for operating the generator.

6. The ozone generator of claim 5 further comprising a plurality of baffles positioned within the lamp section for dispersing the air as the air moves through the lamp section.

7. The ozone generator of claim 6, wherein the air exits the lamp section closer to the second side than where the second UV lamp is positioned relative to the second side.

8. The ozone generator of claim 4 wherein the first and second diameters are determined based on the number of operating UV lamps within the lamp section, the intensity of the UV lamps, and/or the blower speed.

9. The ozone generator of claim 5 wherein the plurality of UV lamps are maintained at a temperature range of 20-25° C. during operation.

10. The ozone generator of claim 5 wherein the air enters the lamp section closer to the first side than where the first UV lamp is positioned relative to the first side.

11. The ozone generator of claim 1 wherein there is a space between each UV lamp of said UV lamps that is at least 2.0 inches.

12. The ozone generator of claim 1, wherein the controller further comprises a switch for turning power on and off, a plurality of UV lamp switches for turning each UV lamp on and off and a timing control unit for automatically turning on power and turning off power to the UV lamps at predetermined times.

13. The ozone generator of claim 1, wherein the ozone generator is configured to produce ozone at a concentration of at least 75 ppm.

14. The ozone generator of claim 1 wherein the controller comprises a timer for controlling when power is supplied to the UV lamps and when power is shut off to the UV lamps.

15. The ozone generator of claim 1, wherein the controller and the application are configured to receive the temperature measurement from the temperature sensor and control the second output device further based on the temperature measurement.

16. The ozone generator of claim 3 further comprising:
a third output device configured to adjust a fan speed of the blower, wherein the controller and application are configured to receive the air measurement from the air sensor and utilize a predetermined algorithm to control the third output device for adjusting the fan speed of the blower based on the air measurement.

17. The ozone generator of claim 16, wherein the air sensor is an air speed sensor and the air measurement is a speed measurement of the air flowing through the UV lamp section.

18. The ozone generator of claim 16, wherein the air sensor is an air volume sensor and the air measurement is a volume measurement of the air flowing through the UV lamp section.

19. The ozone generator of claim 1, wherein the second output device is at least one of an inlet valve and an outlet valve.

* * * * *